US007645450B2

(12) United States Patent
Yoo et al.

(10) Patent No.: US 7,645,450 B2
(45) Date of Patent: Jan. 12, 2010

(54) HUMANIZED ANTIBODY SPECIFIC FOR TUMOR NECROSIS FACTOR-ALPHA

(75) Inventors: Tae Hyoung Yoo, Seoul (KR); Moo Young Song, Suwon-si (KR); Chang Seok Kim, Suwon-si (KR); Sang Koo Park, Yongin-si (KR); Kang In Na, Yongin-si (KR); Byung Kyu Lee, Gunpo-si (KR); Heui Il Kang, Gunpo-si (KR)

(73) Assignee: Yuhan Corporation, Seoul (KR)

( * ) Notice: Subject to any disclaimer, the term of this patent is extended or adjusted under 35 U.S.C. 154(b) by 104 days.

(21) Appl. No.: 11/722,094

(22) PCT Filed: Dec. 29, 2005

(86) PCT No.: PCT/KR2005/004634

§ 371 (c)(1),
(2), (4) Date: Jun. 19, 2007

(87) PCT Pub. No.: WO2006/071091

PCT Pub. Date: Jul. 6, 2006

(65) Prior Publication Data

US 2008/0008703 A1 Jan. 10, 2008

(30) Foreign Application Priority Data

Dec. 29, 2004 (KR) ...................... 10-2004-0115709

(51) Int. Cl.
*A61K 39/395* (2006.01)
(52) U.S. Cl. .............. 424/133.1; 424/145.1; 530/387.3; 530/388.23
(58) Field of Classification Search ........................ None
See application file for complete search history.

(56) References Cited

U.S. PATENT DOCUMENTS 7,196,177 B2 * 3/2007 Kang et al. ............ 530/388.23
2003/0187231 A1 * 10/2003 Le et al. ................. 530/388.15

FOREIGN PATENT DOCUMENTS

KR      2005-47182 A      5/2005
WO      2005/047329 A1    5/2005

OTHER PUBLICATIONS

Janeway et al., Immunobiology, 5th Ed., Garland Science, pp. 94-105 (2001).*
Wang, Z., et al., "Humanization of a mouse monoclonal antibody neutralizing TNF-alpha by guided selection," J. of Immunological Methods, 241, 171-184, 2000.
O'Brien, S., et al., "Humanization of Monoclonal Antibodies by CDR Grafting," Methods in Molecular Biology, 207, 81-100, 'Jan. 1, 2003.
Song M.Y., et al., "Characterization of a novel anti-human TNF-α murine monoclonal antibody with high binding affinity and neutralizing activity," Exper. and Molecular Medicine, 40:1, Feb. 2008, 35-42.
Nagahira, K. et al., "Humanization of a mouse neutralizing monoclonal antibody against tumor necrosis factor-alpha (TNF-alpha)" J. Immunol Methods, 1999, vol. 222(1-2): pp. 83-92.
Tempest, P.R., et al., "A humanized anti-tumor necrosis factor-alpha monoclonal antibody that acts a partial, competitive antagonist of the template antibody," Hybridoma, 1994, vol. 13(3): pp. 183-190.
Doring, E., et al., "Identification and characterization of a TNF alpha antagonist derived from a monoclonal antibody," Mol Immuno, 1994, vol. 31(14): pp. 1059-1067.
Eck, M.J., et al., "The Structure of Human Lymphotoxin (Tumor Necrosis Factor-62 ) at 1.9-Å Resolution," J. Bio. Chem., 267, 4, Feb. 5, 1992, pp. 2119-2122.
Smith, R.A., et al, "The Active Form of Tumor Necrosis Factor Is A Trimer," J. Bio. Chem., 262, 15, May 25, 1987, pp. 6951-6954.
Beyaert, R., et al., "Molecular mechanisms of tumor necrosis factor-induced cytotoxicity What we do understand and what we do not," FEBS Letters 340, 1994, pp. 9-16.
Saklatvala, J., "Tumour necrosis factor α stimulates resorption and inhibits synthesis of proteoglycan in cartilage," Nature, 322, Aug. 7, 1986, pp. 547-549.
Pober, J.S., et al., "Two Distinct Monokines, Interleukin 1 and Tumor Necrosis Factor, Each Independently Induce Biosynthesis and Transient Expression of the Same Antigen on the Surface of Cultured Human Vascular Endothelial Cells," J. Immunology, 136, 5, Mar. 1, 1986, pp. 1680-1687.
Pober, J.S., et al., "Activation of Cultured Human Endothelial Cells by Recombinant Lymphotoxin: Comparison with Tumor Necrosis Factor and Interleukin 1 Species," J. Immunology, 138, 10, May 15, 1987, pp. 3319-3324.
Fiers, W., "Tumor necrosis factor," FEBS Letters, 285, 2, pp. 199-212, Jul. 1991.
Buchan, G., et al., "Interleukin-1 and tumour necrosis factor mRNA expression in rheumatoid arthritis: prolonged production of IL-1α," Clin. Exp. Immunol., 73, 1988, pp. 449-455.
Butler, D.M., et al., "Modulation of proinflammatory cytokine release in rheumatoid synovial membrane cell cultures. Comparison of monoclonal anti TNG-α antibody with the interleukin-1 receptor antagonist," Eur. Cytokine Netw., 6, 4, Jul.-Dec. 1995, pp. 225-230.
Piguet, P.F., et al., "Evolution of collagen arthritis in mice is arrested by treatment with anti-tumour necrosis factor (TNF) antibody or a recombinant soluble TNF receptor," Immunology, 77, 1992, pp. 510-514.

(Continued)

*Primary Examiner*—Ram R Shukla
*Assistant Examiner*—Zachary Skelding
(74) *Attorney, Agent, or Firm*—Sughrue Mion, PLLC

(57) ABSTRACT

Humanized antibodies specifically binding to hTNF-α are prepared from a mouse monoclonal antibody by the CDR (complementarity determining region) grafting method, and they show an antigen binding affinity similar to the original mouse monoclonal antibody and significantly low immunogenicity. Therefore, the humanized antibodies can be effectively used for treating a hTNF-α-related disease such as rheumatoid arthritis, Crohn's disease, psoriatic arthritis, psoriasis, septicemia, asthma, Wegener's granulomatosis, inflammation, and ankylosing spondylitis.

6 Claims, 8 Drawing Sheets

OTHER PUBLICATIONS

Wooley, P.H., et al., "Influence of a Recombinant Human Soluble Tumor Necrosis Factor Receptor FC Fusion Protein on Type II Collagen-Induced Arthritis in Mice," J. of Immunology, 151, 11, Dec. 1, 1993, pp. 6602-6607.

Williams, R.O., et al., "Successful therapy of collagen-induced arthritis with TNF receptor-IgG fusion protein and combination with anti-CD4," Immunology, 84, 1995, pp. 443-439.

Keffer, J., et al., "Transgenic mice expressing human tumour necrosis factor: a predictive genetic model of arthritis," EMBO Journal, 10, 13, 1991, pp. 4025-4031.

Kohler G., et al., "Continuous cultures of fused cells secreting antibody of predefines specificity," Nature, 256, Aug. 7, 1975 pp. 495-497.

Dimaggio J.J., et al., "Monoclonal antibody therapy of cancer," Cancer Chemo. And Bio. Resp. Modifiers Annual 11, 11, 1990, pp. 177-203.

Riechmann L., et al., "Reshaping human antibodies for therapy," Nature, 332, Mar. 24, 1988, pp. 323-327.

Nakatani, T., et al., "Humanization of mouse anti-human IL-2 receptor antibody B-B10," Protein Eng'n, 7, 3, 1994, pp. 435-443.

Carter P., et al., "Humanization of an anti-p185$^{HER2}$ antibody for human cancer therapy," Proc. Natl. Acad. Sci. USA, 89, May 1992, pp. 4285-4289.

\* cited by examiner

FIG. 1

```
TSK114H:QVQLVQSGPE LKKPGETVKI SCKASGYTFT HYGMNWVKQA PGEGLKWMGW INTNTGEPRY
   Hh1:QVQLVQSGAE VKKPGASVKV SCKASGYTFT GYYMHWVRQA PGQGLEWMGW INPNSGGTNY
 TNHV2:QVQLVQSGPE LKKPGASVKV SCKASGYTFT HYGMNWVRQA PGQGLEWMGW INTNTGEPRY
TNHV2k:QVQIVQSGPE LKKPGASVKV SCKASGYTFT HYGMNWVRQA PGKGLEWMGW INTNTGEPRY
TNHV1k:QVQLVQSGPE LKKPGASVKV SCKASGYTFT HYGMNWVRQA PGKGLEWMGW INTNTGEPRY

TSK114H:DEEEKGRFAF SLETSASTAY LQINNLRRED TATYFCARYD SRGEDCWGQG TTLTVSS (SEQ ID NO: 47)
   Hh1:AQKFQGRVTM TRDTSASTAY MELSSLRSED TAVYYCAR--  ------             (SEQ ID NO: 48)
 TNHV2:DEEEKGRVTM TRDTSASTAY MELSSLRSED TAVYYCARYD SRGEDCWGQG TTVTVSS (SEQ ID NO: 36)
TNHV2k:DEEEKGRVTM TRDTSASTAY MELSSLRSED TAVYYCARYD SRGEDCWGQG TTVTVSS (SEQ ID NO: 37)
TNHV1k:DEEFKGRVTM TRDTSASTAY MELSSLRSED TAVYYCARYD SRGEDCWGQG TTLTVSS (SEQ ID NO: 38)
```

FIG. 2

```
TSK114L:QIVLTQSPAI MSASLGERVT MTCTASSSIS YNYFHWYQQR PGSSPKLWIY SSSNLASGVP
   Hk1:QIQMTQSPSS LSASVGDRVT ITCQASQDIS -NYLNWYQQK PGKAPKLLIY DASNLETGVP
 TNLV2:QIVMTQSPSS LSASVGERVT ITCTASSSIS YNYFHWYQQK PGSAPKLWIY SSSNLASGVP
TNLV2d:DIVMTQSPSS LSASVGERVT ITCTASSSIS YNYFHWYQQK PGSAPKLWIY SSSNLASGVP

TSK114L:PRISGSGSGT SYSLTISSME AEDAATYYCH QYERSPWTFG GGTKLEIKR (SEQ ID NO: 49)
   Hk1:SRFSGSGSGT DFTFTISSLQ PEDIATYYCQ QYDNLP-               (SEQ ID NO: 50)
 TNLV2:SRESGSGSGT DFTFTISSLQ PEDIATYYCH QYERSPWTFG GGTKVEIKR (SEQ ID NO: 39)
TNLV2d:SRFSGSGSGT DFTFTISSLQ PEDIATYYCH QYERSPWTFG GGTKVEIKR (SEQ ID NO: 40)
```

1. Humanized Ab YHB1406
2. Humanized Ab YHB1411
3. Protein size marker
4. Protein size marker
5. Humanized Ab YHB1406-2
6. Humanized Ab YHB1411-2

HUMANIZED ANTIBODY SPECIFIC FOR TUMOR NECROSIS FACTOR-ALPHA

This is a National Stage application under 35 U.S.C. § 371 of PCT/KR2005/004634 filed Dec. 29, 2005 and which claims priority from Korean Paten Application 10-2004-0115709 filed Dec. 29, 2004, which are incorporated herein by reference.

FIELD OF THE INVENTION

The present invention relates to a humanized antibody specific for human tumor necrosis factor-α, and a method for the preparation thereof.

BACKGROUND OF THE INVENTION

Human tumor necrosis factor-α (hereinafter, referred to as "hTNF-α") is a homotrimer consisting of three 17 kDa protein subunits (Eck M. J. et al., JBC, 267: 2119-2122, 1992; Smith R. A. et al., JBC, 262: 6951-6954, 1987). hTNF-α is an inflammatory cytokine secreted from macrophages and monocytes, and functions as a signal transmitter in several cellular reactions such as necrosis and apoptosis (Beyaert R. et al., FEBS Lett., 340: 9-16, 1994). hTNF-α causes a pro-inflammatory action leading to tissue destruction, such as breakdown of the cartilage and bone (Saklatvala, Nature, 322: 547-549, 1986), induction of an adhesion molecules, induction of procoagulation activity in vascular endothelial cells (Pober J S et al., J. Immunol., 136; 1680-1687, 1986), and increase in the adherence of neutrophils and lymphocytes (Pober et al., J. Immunol. 138: 3319-3324, 1987). In addition, it has been known that hTNF-α plays an important role in a defense mechanism against infectious disease and tumor (Fiers W., FEBS Lett., 285: 199-212, 1991).

hTNF-α is involved in inflammatory diseases, autoimmune diseases, bacterial infections, cancers and degenerative diseases. Among these diseases, hTNF-α has been regarded as a useful target protein for a specific physiological treatment of rheumatoid arthritis, Crohn's disease, psoriatic arthritis, and ankylosing spondylitis.

Meanwhile, it has been also suggested to use a hTNF-α inhibitor for the purpose of treating rheumatoid arthritis. It has been reported that hTNF-α is overexpressed in the synovial cells isolated from the early-stage rheumatoid joint (Buchan G. et al., Clin. Exp. Immunol., 73: 449-455, 1988), and cytokines relating to rheumatoid arthritis lesions are decreased when the above synovial cells are treated with an anti-hTNF-α monoclonal antibody (Butler D. M. et al., Eur. Cytokine Netw., 6: 225-230, 1995). Further, it has been found that an anti-hTNF-α antibody or a recombinant soluble hTNF-α receptor suppresses inflammation and destruction of a joint in a collagen induced mouse arthritis model (Piguet P. F. et al., Immunology, 77: 510-514, 1992; Wooley P. H. et al., J. Immunol., 151: 6602-6607, 1993; Williams R. O. et al., Immunology, 84: 433-439, 1995). Moreover, it has been observed that inflammatory arthritis is induced in a transgenic mouse overexpressing hTNF-α (Keffer J. et al., EMBO J., 10: 4025-4031, 1991).

These results indicate that hTNF-α plays an important role as a direct or indirect regulator controlling inflammatory cytokines in rheumatoid athritis. Accordingly, there has been a need to develop a monoclonal antibody having high selectivity and reactivity to hTNF-α for the purpose of treating rheumatoid arthritis.

Generally, an antibody having high selectivity and reactivity to a specific antigen is prepared through immunization of a mouse with the antigen (Kohler G. & Milstein C., Nature, 256; 495-497, 1975). A mouse monoclonal antibody is advantageous in that it is easy to prepare the antibody and to select an antibody having a high reactivity. However, it also has a problem that an anti-mouse antibody is formed in a human body when it is administered for a long time (Dimaggio J. J., et al., Cancer Chemother. Biol. Response Modif., 11: 177-203, 1990).

To overcome the undesirable properties of mouse monoclonal antibodies, a humanized antibody has been developed by replacing the framework regions except for the antigen-binding site with those of a human antibody. As a method for preparing such humanized antibody, a CDR (complementarity determining region) grafting method is currently employed, wherein only the CDRs of a mouse antibody are grafted to a human antibody. The humanized antibody prepared by CDR grafting has an advantage of reducing in vivo immune responses (Riechmann et al., Nature, 332: 323, 1988; Nakatani et al., Protein Engineering, 7: 435, 1994), however, it often loses the high selectivity and reactivity of the original mouse antibody (Carter P., et al., Proc. Natl. Acad. Sci. USA, 89: 4285-4289, 1992).

The present inventors have endeavored to overcome such problems of the conventional humanized antibody, and developed a novel humanized antibody specifically binding to hTNF-α, which shows an antigen binding affinity similar to that of the original mouse monoclonal antibody and minimized immunogenicity.

SUMMARY OF THE INVENTION

Accordingly, it is an object of the present invention to provide a humanized antibody specific for hTNF-α.

It is another object of the present invention to provide a DNA encoding the heavy or light chain of the humanized antibody, and an expression vector comprising the DNA.

It is a further object of the present invention to provide a microorganism transformed with the expression vector.

It is a still further object of the present invention to provide a pharmaceutical composition for treating a diseases relating to hTNF-α, comprising the humanized antibody as an effective ingredient.

In accordance with one aspect of the present invention, there is provided a humanized antibody specific for hTNF-α, which comprises:

a) a heavy chain variable region having the following amino acid sequences for complementarity determining regions, respectively,

HYGMN WINTNTGEPRYDEEFKG YDSRGFDC (SEQ ID NO: 41 to 43);

b) a light chain variable region having the following amino acid sequences for complementarity determining regions, respectively,

TASSSISYNYFH SSSNLAS HQYERSPWT (SEQ ID NO: 44 to 46);

c) a heavy chain constant region identical to that of a human antibody; and d) a light chain constant region identical to that of a human antibody.

BRIEF DESCRIPTION OF THE DRAWINGS

The above and other objects and features of the present invention will become apparent from the following description of the invention, when taken in conjunction with the accompanying drawings, which respectively show:

FIG. 1: Comparison of the amino acid sequences of the heavy chain (TSK114 H) variable region of a mouse monoclonal antibody specifically binding to TNF-α (SEQ ID NO: 47), heavy chain subgroup 1 (Hh1) of a human antibody (SEQ ID NO: 48), and the heavy chains (TNHV2, TNHV2k and TNHV1k) of the humanized antibodies of the present invention (SEQ ID NOs: 36 to 38);

FIG. 2: Comparison of the amino acid sequences of the light chain (TSK114 L) of a mouse monoclonal antibody specifically binding to TNF-α (SEQ ID NO: 49), light chain subgroup 1 (Hk1) of a human antibody (SEQ ID NO: 50), and the light chains (TNLV2 and TNLV2d) of the humanized antibodies of the present invention (SEQ ID NOs: 39 and 40);

DETAILED DESCRIPTION OF THE INVENTION

Figure 3:
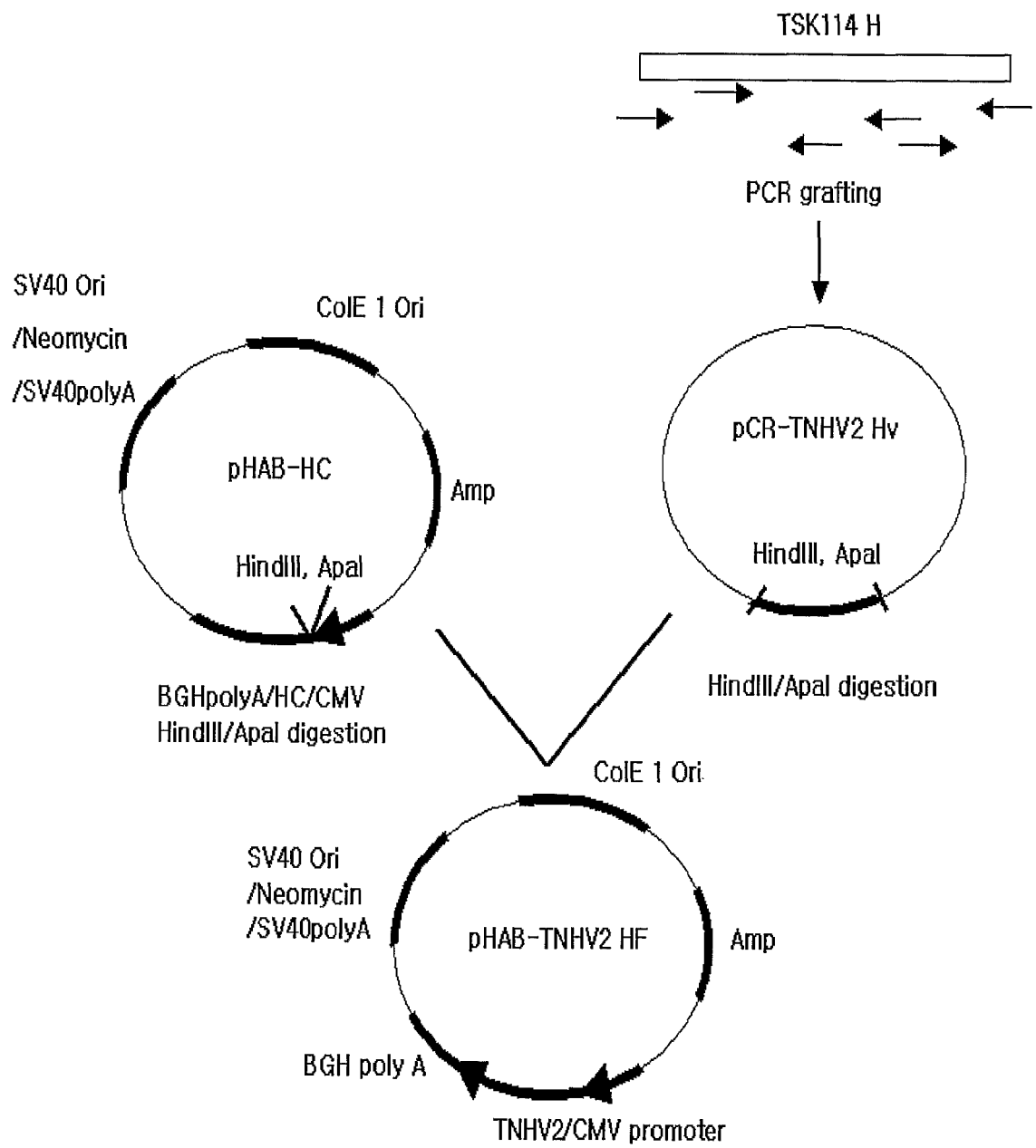
FIG. 3: Schematic diagram showing the process for preparing vector pHAB-TNHV2 HF expressing the heavy chain of the inventive humanized antibody.

In the humanized antibodies of the present invention, the CDRs in the heavy and light chain variable regions thereof are derived from a mouse monoclonal antibody, and the framework regions except for the CDRs as well as the heavy and light chain constant regions are derived from a human antibody. Preferably, the inventive humanized antibody exhibits an antigen binding affinity (Kd) ranging from $1 \times 10^{-9}$ M to $1 \times 10^{-13}$ M. Further, the dissociation constant ($K_{off}$) of the inventive humanized antibody ranges from $1 \times 10^{-6}$ s$^{-1}$ to $1 \times 10^{-9}$ s$^{-1}$, when determined by surface plasmon resonance (SPR).

The humanized antibody of the present invention can be prepared by a CDR grafting method from the mouse monoclonal antibody TSK114 (Deposit Accession Nos: KCTC 10514BP and KCTC 10515BP) specific for hTNF-α, wherein the heavy chain variable region of the mouse monoclonal antibody TSK114 comprises three CDRs of SEQ ID NOs: 41 to 43, and the light chain variable region, three CDRs of SEQ ID NOs: 44 to 46.

First, the amino acid sequences of the light chain and heavy chain variable regions of mouse monoclonal antibody are compared with human sequences in the GenBank database, and selected are the human heavy chain variable region subgroup 1 (Hh1) as defined by Kabat having the greatest sequence similarity to the mouse antibody heavy chain and the human light chain kappa variable region subgroup 1 (Hk1) having the most similarity to the mouse antibody light chain (Harris L. & Bajorath J., *Protein Science,* 4; 306-310, 1995).

The genes encoding heavy and light chains of the humanized antibody can be amplified by using these selected human genes as templates. In this procedure, each of the nucleotide sequences encoding the heavy and light chains of the humanized antibody may be modified based on the information of well-known genetic studies and antibody structural analyses. Further, if certain amino acid residues of the mouse monoclonal antibody affect the antigen binding affinity or they are important for maintaining the antibody structure, it is preferable to preserve the nucleotide sequences encoding the amino acid residues without modification (Kabat E. A. et al., *D.H.H.S. Publication number (NIH)* 91-3242, 1991; Chothia C. et al., *Nature,* 342; 877-883, 1989; Studnicka G. M. et al., *Protein Engineering,* 7; 805-814, 1994 ; Harris L. & Bajorath J., *Protein Science,* 4; 306-310, 1995).

A gene encoding the heavy chain variable region of the humanized antibody may be prepared by replacing the framework regions except for the antigen-binding site in the heavy chain variable region of the mouse monoclonal antibody TSK114 specifically binding to hTNF-α with the heavy chain subgroup 1 (Hh1) of a human antibody. Such a gene encoding the heavy chain variable region of the humanized antibody can be prepared by the steps of: designing primers for humanizing the mouse monoclonal antibody using the gene encoding the heavy chain of mouse monoclonal antibody TSK114 as a template; performing PCR (polymerase chain reaction) using the corresponding primers; and ligating the so-amplified PCR products to each other using restriction enzymes and DNA ligase. The genes encoding the heavy chain variable region of the humanized antibody thus prepared have been designated TNHV2 (SEQ ID NO: 31), TNHV2k (SEQ ID NO: 32), and TNHV1k (SEQ ID NO: 33), which encode the polypeptides having the amino acid sequences of SEQ ID NOs: 36, 37 and 38, respectively (see FIG. 1).

In order to prepare a gene encoding the full-length heavy chain of the humanized antibody including the gene encoding the humanized heavy chain variable region, gene TNHV2, TNHV2k or TNHV1k is inserted into an appropriate vector, e.g., TOPO vector (TOPO TA cloning kit, Invitrogen, US), to prepare expression vectors pCR-TNHV2 Hv, pCR-TNHV2k Hv and pCR-TNHV1k Hv. A gene fragment encoding the heavy chain variable region of the humanized antibody is isolated from the expression vector pCR-TNHV2 Hv, pCR-TNHV2k Hv or pCR-TNHV1k Hv, and inserted into vector pHAB-HC (Deposit Accession No: KCTC 10229BP; Korean Patent Laid-open Publication No: 2004-12266) containing the gene encoding the heavy chain constant region of a human antibody, to obtain expression vector of the humanized antibody heavy chain. Expression vectors thus prepared have been designated pHAB-TNHV2 HF, pHAB-TNHV2k HF, and pHAB-TNHV1k HF.

*E. coli* TOP10F' transformants transformed with the expression vectors pHAB-TNHV2 HF and pHAB-TNHV2k HF were deposited on Sep. 1, 2004 with the Korean Collection for Type Cultures (KCTC) (Address: Korea Research Institute of Bioscience and Biotechnology (KRIBB), #52, Oun-dong, Yusong-ku, Taejon, 305-333, Republic of Korea) under the accession numbers KCTC 10691BP and KCTC 10692BP, respectively, and an *E. coli* TOP10F' transformant transformed with the expression vector pHAB-TNHV1k HF was deposited on Jun. 13, 2005 with KCTC under the accession number KCTC 10818BP, in accordance with the terms of Budapest Treaty on the International Recognition of the Deposit of Microorganisms for the Purpose of Patent Procedure.

The genes encoding the full-length heavy chain of the humanized antibody can be isolated from the heavy chain expression vectors pHAB-TNHV2 HF, pHAB-TNHV2k HF, and pHAB-TNHV1k HF, and have been designated TNHV2 HF, TNHV2k HF and TNHV1k HF, respectively.

A gene encoding the light chain variable region of the humanized antibody may be prepared by replacing the framework regions except for the antigen-binding site in the light chain variable region of the mouse monoclonal antibody TSK114 specifically binding to hTNF-α with the light chain subgroup 1 (Hk1) of a human antibody. Such a gene encoding the light chain variable region of the humanized antibody can be prepared by the steps of: designing primers for humanizing the mouse monoclonal antibody using the gene encoding the light chain of mouse monoclonal antibody TSK114 as a template; performing PCR using the corresponding primers; and ligating the so-amplified PCR products to each other using restriction enzymes and DNA ligase. The genes encoding the light chain variable region of the humanized antibody thus prepared have been designated TNLV2 and TNLV2d, which encode the polypeptides having the amino acid sequences of SEQ ID NOs: 39 and 40, respectively (see FIG. 2).

In order to prepare a gene encoding the full-length light chain of the humanized antibody including the gene encoding the humanized light chain variable region, gene TNLV2 or TNLV2d is inserted into an appropriate vector, e.g., TOPO vector, to prepare expression vectors pCR-TNLV2 Lv and pCR-TNLV2d Lv. A gene fragment encoding the light chain variable region of the humanized antibody is isolated from the expression vector pCR-TNLV2 Lv or pCR-TNLV2d Lv, and inserted into vector pHAB-KC (Deposit Accession No: KCTC 10230BP; Korean Patent Laid-open Publication No: 2004-12268) containing the gene encoding the light chain constant region of a human antibody, to obtain expression vector of the humanized antibody light chain. Expression vectors thus prepared have been designated pHAB-TNLV2 LF and pHAB-TNLV2d LF.

An *E. coli* TOP10F' transformant transformed with the expression vector pHAB-TNLV2 LF was deposited on Sep. 1, 2004 with KCTC under the accession number KCTC 10690BP, and an *E. coli* TOP10F' transformant transformed with the expression vector pHAB-TNLV2d LF was deposited on Jun. 13, 2005 with KCTC under the accession number KCTC 10817BP, in accordance with the terms of Budapest Treaty on the International Recognition of the Deposit of Microorganisms for the Purpose of Patent Procedure.

The genes encoding the full-length light chain of the humanized antibody can be isolated from the light chain expression vectors pHAB-TNLV2 LF and pHAB-TNLV2d LF, and have been designated TNLV2 LF and TNLV2d LF, respectively.

CHO cell lines may be transformed with humanized heavy chain expression vector pHAB-TNHV2 HF and humanized light chain expression vector pHAB-TNLV2 LF by using an appropriate transformation solution such as GenePORTER (GTS, US) to obtain a transformant producing the humanized antibody specific for hTNF-α, and the transformant has been designated CHO-YHB1406. Further, another transformant may be prepared by using humanized heavy chain expression vector pHAB-TNHV2k HF and humanized light chain expression vector pHAB-TNLV2 LF or pHAB-TNLV2d LF according to the same method as described above. These transformants have been designated CHO-YHB1411 and CHO-YHB1411-2. In addition, another transformant may be prepared by using humanized heavy chain expression vector pHAB-TNHV1k HF and humanized light chain expression vector pHAB-TNLV2d LF according to the same method as described above, and has been designated CHO-YHB1406-2.

To purify the humanized antibody of the present invention from the transformant cell lines, the transformant CHO-YHB1406, CHO-YHB1411, CHO-YHB1411-2 or CHO-YHB1406-2 may be cultured in an appropriate culture medium, and the culture supernatant may be subjected to column chromatography using Protein-A (Amersham Bioscience, Sweden) or goat anti-human immunoglobulin G (Zymed Laboratories Inc., USA). The humanized antibodies thus purified have been designated YHB1406, YHB1411, YHB1411-2 and YHB1406-2, respectively.

The antigen binding affinity of the humanized antibody may be determined by, e.g., competitive ELISA, solid phase ELISA or surface plasma resonance. Humanized antibodies YHB1406, YHB1411, YHB1411-2 and YHB1406-2 specifically binding to hTNF-α show antigen-binding affinities ranging from $1\times10^{-9}$ M to $1\times10^{-13}$ M, which demonstrates that the humanized antibodies of the present invention have antigen-binding activities similar to that of the original mouse monoclonal antibody, while showing significantly decreased immunogenicity, and therefore, may be effectively used for treating hTNF-α related diseases. Further, the dissociation constant ($K_{off}$) of the inventive humanized antibody determined by SPR ranges from $1\times10^{-6}$ s$^{-1}$ to $1\times10^{-9}$ s$^{-1}$, which reflects a very low degree of dissociation of the antigen-antibody complex.

For this purpose, the humanized antibody of the present invention may be used as an effective ingredient in a pharmaceutical composition to treat a hTNF-α related disease such as rheumatoid arthritis, Crohn's disease, psoriatic arthritis, psoriasis, septicemia, asthma, Wegener's granulomatosis, inflammation and ankylosing spondylitis.

The compositions of the present invention may be formulated so as to provide quick, sustained or delayed release of the effective ingredient after administration to a patient by employing any one of the procedures well known in the art. The composition may comprise pharmaceutically acceptable excipients, diluents, fillers, disintegrants, sweeteners, lubricants, and flavors. The pharmaceutical composition is preferably formulated for intravenous administration, either by bolus injection or sustained drip, or for release from an implanted capsule. A typical formulation for intravenous administration utilizes physiological saline as a diluent.

The dose of the antibody actually administered to a patient ought to be determined in light of various relevant factors including the specific antibody to be administered, administration time and formulation of the composition, route of administration, the disease to be treated, and body weight, age, gender, state of health and diet of a patient. A typical dose may range from 0.01 mg/kg/day to 1,000 mg/kg/day. More typically, the dose may range from 0.1 mg/kg/day to 10 mg/kg/day.

The following Examples are intended to further illustrate the present invention without limiting its scope.

EXAMPLE 1

Construction of a Gene Encoding a Heavy Chain Variable Region of a Humanized Antibody PCR was conducted using a gene encoding the heavy chain variable region of the mouse monoclonal antibody TSK114 (Deposit Accession Nos: KCTC 10514BP and KCTC 10515BP) specific for TNF-α as a template and a primer pair of SEQ ID NOs: 1 and 14, to amplify gene A encoding the heavy chain variable region of the humanized antibody carrying a leader sequence. The amplified PCR product was electrophoresed on an agarose gel and recovered from the gel using QIAgel extraction kit (Qiagen, USA).

Gene A thus obtained was subjected to PCR with a primer pair of SEQ ID NOs: 1 and 7 or SEQ ID NOs: 6 and 14 to amplify DNA fragments, and overlapping PCR was performed using the resulting DNA fragments with a primer pair of SEQ ID NOs: 1 and 14. The amplified PCR product was incubated with TOPO vector (TOPO TA cloning kit, Invitrogen Inc., USA) at room temperature for 45 min to be cloned, and the cloned vector was transformed into *E. coli* TOP10F' (Invitrogen Inc., USA). After incubating the transformed *E. coli* in LB media containing 100 μg/ml of ampicilline, plasmid was isolated from the *E. coli*, and digested with EcoRI (BioLabs Inc., USA) to prepare about 450 bp gene B encoding the heavy chain variable region.

PCR was performed using gene B as a template and a primer pair of SEQ ID NOs: 1 and 9 or SEQ ID NOs: 8 and 14 to amplify DNA fragments, and overlapping PCR was performed using the resulting DNA fragments with a primer pair of SEQ ID NOs: 1 and 14. In the same manner as described above, the amplified PCR product was cloned in TOPO vector, and digested with EcoRI to prepare gene C encoding the heavy chain variable region.

In the same manner as described above, gene C was subjected to PCR with a primer pair of SEQ ID NOs: 1 and 11 or SEQ ID NOs: 10 and 14 to amplify DNA fragments, and overlapping PCR was performed using the resulting DNA fragments with a primer pair of SEQ ID NOs: 1 and 14. The PCR product thus amplified was cloned in TOPO vector to obtain gene D encoding the heavy chain variable region. Gene D was subjected to PCR with a primer pair of SEQ ID NOs: 4 and 14 or SEQ ID NOs: 1 and 5 to amplify DNA fragments, and overlapping PCR was performed using the resulting DNA fragments with a primer pair of SEQ ID NOs: 1 and 14. In the same manner as described above, the PCR product thus amplified was cloned in TOPO vector obtain gene E encoding the heavy chain variable region.

Further, PCR was conducted using gene E as a template and a primer pair of SEQ ID NOs: 1 and 3 or SEQ ID NOs: 2 and 14 to amplify DNA fragments, and overlapping PCR was performed using the resulting DNA fragments with a primer pair of SEQ ID NOs: 1 and 14. In the same manner as described above, the PCR product was cloned in TOPO vector to obtain gene TNHV2 (SEQ ID NO: 31) encoding the heavy chain variable region, and the TOPO vector inserted with TNHV2 was designated pCR-TNHV2 Hv.

In the same manner as described above, PCR was conducted using TNHV2 as a template and a primer pair of SEQ ID NOs: 1 and 13 or SEQ ID NO: 12 and 14 to amplify DNA fragments, and overlapping PCR was performed using the resulting DNA fragments with a primer pair of SEQ ID NOs: 1 and 14. The PCR product was cloned in TOPO vector to obtain another gene encoding the heavy chain variable region. The gene was designated TNHV2k (SEQ ID NO: 32), and the TOPO vector inserted with gene TNHV2k was designated pCR-TNHV2k Hv.

Further, in the same manner as described above, PCR was conducted using gene TNHV2k as a template and a primer pair of SEQ ID NOs: 1 and 15, and the PCR product was cloned in TOPO vector to obtain still another gene encoding the heavy chain variable region. The gene was designated TNHV1k (SEQ ID NO: 33), and the TOPO vector inserted with TNHV1k was designated pCR-TNHV1k Hv.

The primer pairs and reaction conditions employed in each PCR reaction are shown in Table 1. Each PCR reaction was conducted under the following conditions of 30 cycles as shown in Table 1 after initial denaturation of 7 min at 95° C., and final extension of 10 min at 72° C.

TABLE 1

| Primer pair | Gene | PCR condition | | |
|---|---|---|---|---|
| | | Denaturation | Annealing | Extension |
| SEQ ID NOs: 1 and 14 | A | 95° C., 2 min | 58° C., 1.5 min | 72° C., 2 min |
| SEQ ID NOs: 6 and 14 | B | 95° C., 2 min | 58° C., 1.5 min | 72° C., 2 min |
| SEQ ID NOs: 1 and 7 | | 95° C., 2 min | 58° C., 1.5 min | 72° C., 2 min |
| SEQ ID NOs: 5 and 14 | C | 95° C., 2 min | 58° C., 1.5 min | 72° C., 2 min |
| SEQ ID NOs: 1 and 9 | | 95° C., 2 min | 58° C., 1.5 min | 72° C., 2 min |
| SEQ ID NOs: 10 and 14 | D | 95° C., 2 min | 58° C., 1.5 min | 72° C., 2 min |
| SEQ ID NOs: 1 and 11 | | 95° C., 2 min | 58° C., 1.5 min | 72° C., 2 min |
| SEQ ID NOs: 4 and 14 | E | 95° C., 2 min | 58° C., 1.5 min | 72° C., 2 min |
| SEQ ID NOs: 1 and 5 | | 95° C., 2 min | 58° C., 1.5 min | 72° C., 2 min |
| SEQ ID NOs: 2 and 14 | TNHV2 | 95° C., 2 min | 58° C., 1.5 min | 72° C., 2 min |
| SEQ ID NOs: 1 and 3 | | 95° C., 2 min | 58° C., 1.5 min | 72° C., 2 min |
| SEQ ID NOs: 12 and 14 | TNHV2k | 95° C., 2 min | 58° C., 1.5 min | 72° C., 2 min |
| SEQ ID NOs: 1 and 13 | | 95° C., 2 min | 58° C., 1.5 min | 72° C., 2 min |
| SEQ ID NOs: 1 and 15 | TNTJV1k | 95° C., 2 min | 58° C., 1.5 min | 72° C., 2 min |

EXAMPLE 2

Construction of a Full-Length Heavy Chain Gene of a Humanized Antibody and an Expression Vector Thereof In order to construct the gene encoding the humanized full-length heavy chain using the gene encoding the heavy chain variable region inserted in pCR-TNHV2 Hv vector prepared in Example 1, pHAB-HC (KCTC 10229BP, Korean Patent Laid-open Publication No. 2004-12266) vector containing the gene encoding the heavy chain constant region of the human antibody was employed.

First, in order to insert gene TNHV2 encoding the heavy chain variable region of the humanized antibody into expression vector pHAB-HC, pCR-TNHV2 Hv was treated with HindIII/ApaI (BioLabs, Inc., USA) at 37° C. for 2 hrs, electrophoresed on a 1.5% agarose gel and stained with etidium bromide (EtBr), and an about 450 bp fragment of the gene was observed.

Also, pHAB-HC was treated with HindIII/ApaI, eletrophoresed and stained, and an about 6.5 kb fragment of the digested vector was observed. After then, the gene fragments observed were recovered from the gels using a QIAgel extraction kit (Qiagen, USA), treated with T4 DNA ligase (Bio Labs, Inc., USA) at 16° C. overnight, and transformed into *E. coli* TOP10F' to obtain a transformant. The transformant was cultured in an LB medium supplemented with 100 µg/ml of ampicillin overnight, and a plasmid was isolated therefrom. The isolated plasmid was treated with HindIII/NotI and subjected to agarose gel electrophoresis, to obtain an about 1.4 kb full-length heavy chain gene of the humanized antibody.

The full-length heavy chain gene of the humanized antibody thus prepared was designated TNHV2 HF. Further, the expression vector inserted with TNHV2 HF was designated pHAB-TNHV2 HF (FIG. 3), and transformed into *E. coli* TOP10F' to obtain a transformant, which was deposited on Sep. 1, 2004 with the Korean Collection for Type Cultures (KCTC) (Address: Korea Research Institute of Bioscience and Biotechnology (KRIBB), #52, Oun-dong, Yusong-ku, Taejon, 305-333, Republic of Korea) under the accession number KCTC 10691BP.

Figure 4:
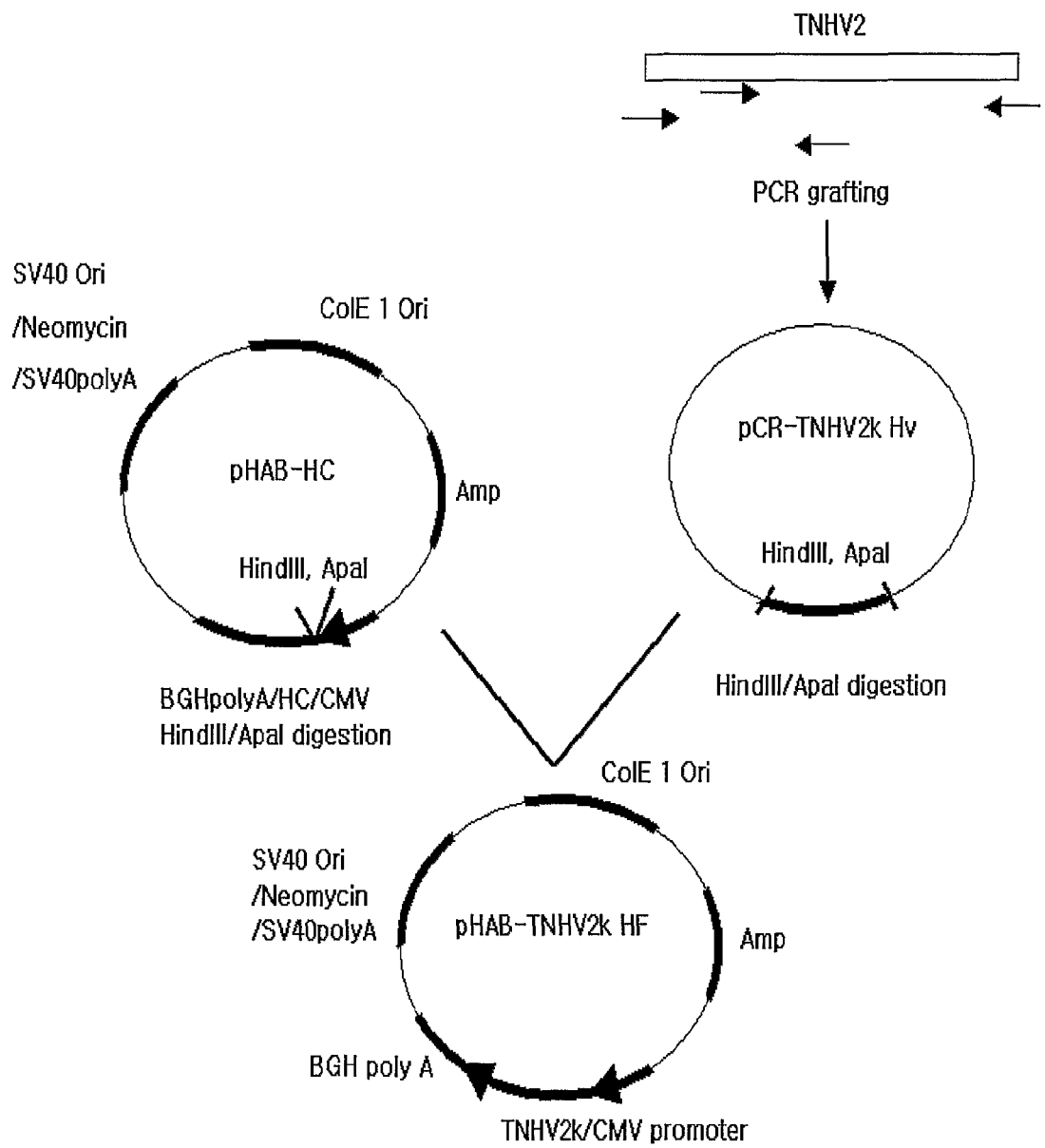
FIG. 4: Schematic diagram showing the process for preparing vector pHAB-TNHV2k HF expressing the heavy chain of the inventive humanized antibody.
Figure 5:
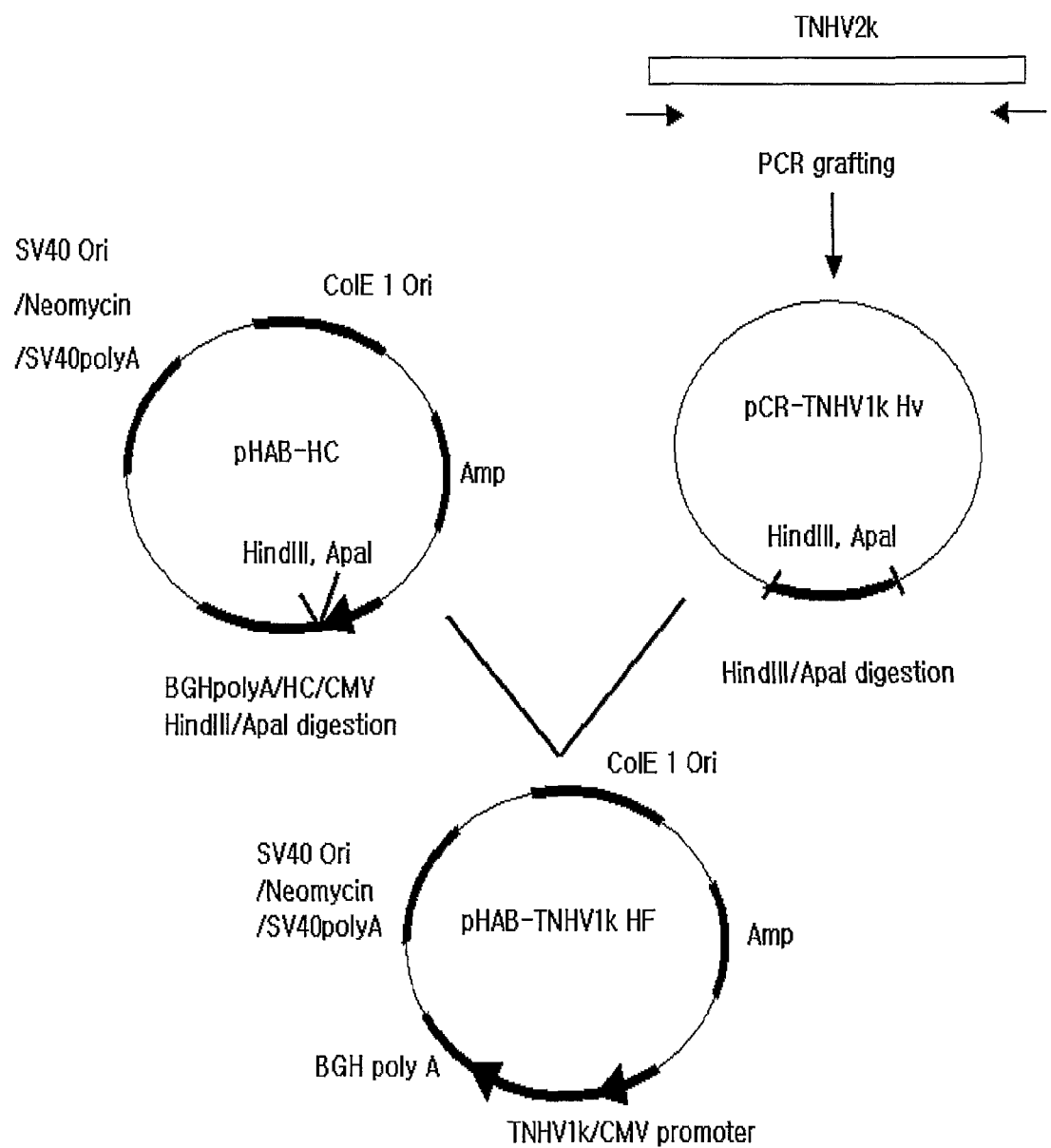
FIG. 5: Schematic diagram showing the process for preparing vector pHAB-TNHV1k HF expressing the heavy chain of the inventive humanized antibody.

In the same manner as described above, the full-length heavy chain gene of the humanized antibody was also prepared using TNHV2k or TNHV1k genes, and the full-length heavy chain genes of the humanized antibody thus prepared were designated TNHV2k HF or TNHV1k HF, respectively. Further, the heavy chain expression vector of the humanized antibody inserted with the full-length heavy chain gene, TNHV2k HF or TNHV1k HF, was designated pHAB-TNHV2k HF or pHAB-TNHV1k HF (FIGS. 4 and 5), respectively, and the *E. coli* TOP10F' transformed with pHAB-TNHV2k HF or pHAB-TNHV1k HF was deposited on Sep. 1, 2004 or Jun. 13, 2005, respectively, with the Korean Collection for Type Cultures (KCTC) under the accession numbers KCTC 10692BP and KCTC 10818BP, respectively.

EXAMPLE 3

Construction of a Gene Encoding a Light Chain Variable Region of a Humanized Antibody PCR was conducted using the gene encoding the light chain variable region of mouse monoclonal antibody TSK114 specifically recognizing TNF-α as a template and a primer pair of SEQ ID NOs: 16 and 30, to amplify gene A encoding the light chain variable region containing a leader sequence. Gene A was subjected to agarose gel electrophoresis and EtBr staining, and recovered from the gel using a QIAgel extraction kit.

Gene A thus purified was subjected to PCR with a primer pair of SEQ ID NOs: 16 and 25 or SEQ ID NOs: 24 and 30 to amplify DNA fragments, and overlapping PCR was performed using the resulting DNA fragments with a primer pair of SEQ ID NOs: 16 and 30. The amplified PCR product was incubated with TOPO vector (TOPO TA cloning kit, Invitrogen Inc., USA) at room temperature for 45 min, and the cloned vector was transformed into *E. coli* TOP10F' to obtain a transformant. After incubating the transformant in LB media containing 100 µg/ml of ampicilline overnight, plasmid was isolated from the *E. coli*, and digested with EcoRI (BioLabs Inc., USA) to obtain about 400 bp gene B encoding the light chain variable region.

PCR was conducted using gene B as a template and a primer pair of SEQ ID NOs: 26 and 30 or SEQ ID NOs: 16 and 27 to amplify DNA fragments, and overlapping PCR was performed using the resulting DNA fragments with a primer pair of SEQ ID NOs: 16 and 30. In the same manner as described above, the amplified PCR product was cloned in TOPO vector, and digested with EcoRI to prepare gene C encoding the light chain variable region.

In the same manner as described above, gene C was subjected to PCR with a primer pair of SEQ ID NOs: 16 and 23 or SEQ ID NOs: 22 and 30 to amplify DNA fragments, and overlapping PCR was performed using the resulting DNA fragments with a primer pair of SEQ ID NOs: 16 and 30. In the same manner as described above, the PCR product thus amplified was cloned in TOPO vector to obtain gene D encoding the light chain variable region.

Gene E encoding the light chain variable region was obtained by performing PCR using gene D as a template with a primer pair of SEQ ID NOs: 18 and 30 or SEQ ID NOs: 16 and 19 to amplify DNA fragments, and overlapping PCR was performed using the resulting DNA fragments with a primer pair of SEQ ID NOs: 16 and 30. In the same manner as described above, the PCR product thus amplified was cloned in TOPO vector.

Gene F encoding the light chain variable region was obtained by performing PCR using gene E as a template with a primer pair of SEQ ID NOs: 20 and 30 or SEQ ID NOs: 16 and 21 to amplify DNA fragments, and overlapping PCR was performed using the resulting DNA fragments with a primer pair of SEQ ID NOs: 16 and 30. In the same manner as described above, the PCR product thus amplified was cloned in TOPO vector.

Further, PCR was conducted using gene F as a template and a primer pair of SEQ ID NOs: 28 and 30 or SEQ ID NOs: 16 and 29 to amplify DNA fragments, and overlapping PCR was performed using the resulting DNA fragments with a primer pair of SEQ ID NOs: 16 and 30. In the same manner as described above, the PCR product was cloned in TOPO vector to obtain gene TNLV2 (SEQ ID NO: 34) encoding the light chain variable region, and the TOPO vector inserted with gene TNLV2 was designated pCR-TNLV2 Lv.

Further, in the same manner as described above, PCR was conducted using TNHV2 as a template and a primer pair of SEQ ID NOs: 16 and 17 to amplify DNA fragment, and the fragment was subjected to PCR using a primer of SEQ ID NOs: 30 as a megaprimer to obtain a gene encoding the light chain variable region of the humanized antibody. The gene was designated TNLV2d (SEQ ID NO: 35), and the TOPO vector inserted with TNLV2d was desinated pCR-TNLV2d Lv.

The primer pairs and PCR conditions employed in the above PCR reactions are described in the following Table 2. Each of the PCR reactions was conducted under the conditions of 30 cycles as shown in Table 2 after initial denaturation of 7 min at 95° C., and final extension of 10 minutes at 72° C.

mented with 100 μg/ml of ampicillin overnight, and a plasmid was isolated from the culture medium. The isolated plasmid was treated with HindIII/NotI (BioLabs, Inc., USA) and subjected to agarose gel electrophoresis, to obtain an about 0.7 lab full-length light chain gene of the humanized antibody.

TABLE 2

| Primer pair | Gene | PCR condition | | |
|---|---|---|---|---|
| | | Denaturation | Annealing | Extension |
| SEQ ID NOs: 16 and 30 | A | 95° C., 2 min | 58° C., 1.5 min | 72° C., 2 min |
| SEQ ID NOs: 24 and 30 | B | 95° C., 2 min | 58° C., 1.5 min | 72° C., 2 min |
| SEQ ID NOs: 25 and 16 | | 95° C., 2 min | 58° C., 1.5 min | 72° C., 2 min |
| SEQ ID NOs: 26 and 30 | C | 95° C., 2 min | 58° C., 1.5 min | 72° C., 2 min |
| SEQ ID NOs: 27 and 16 | | 95° C., 2 min | 58° C., 1.5 min | 72° C., 2 min |
| SEQ ID NOs: 22 and 30 | D | 95° C., 2 min | 58° C., 1.5 min | 72° C., 2 min |
| SEQ ID NOs: 23 and 16 | | 95° C., 2 min | 58° C., 1.5 min | 72° C., 2 min |
| SEQ ID NOs: 18 and 30 | E | 95° C., 2 min | 58° C., 1.5 min | 72° C., 2 min |
| SEQ ID NOs: 19 and 16 | | 95° C., 2 min | 58° C., 1.5 min | 72° C., 2 min |
| SEQ ID NOs: 20 and 30 | F | 95° C., 2 min | 58° C., 1.5 min | 72° C., 2 min |
| SEQ ID NOs: 21 and 16 | | 95° C., 2 min | 58° C., 1.5 min | 72° C., 2 min |
| SEQ ID NOs: 28 and 30 | TNLV2 | 95° C., 2 min | 58° C., 1.5 min | 72° C., 2 min |
| SEQ ID NOs: 29 and 16 | | 95° C., 2 min | 58° C., 1.5 min | 72° C., 2 min |
| SEQ ID NOs: 16 and 17 | TNLV2d | 95° C., 2 min | 58° C., 1.5 min | 72° C., 2 min |
| SEQ ID NO: 30 | | 95° C., 2 min | 58° C., 1.5 min | 72° C., 2 min |

EXAMPLE 4

Construction of a Full-Length Light Chain Gene of a Humanized Antibody and an Expression Vector Thereof In order to construct the gene encoding the hum anized full-length light chain using the gene encoding the light chain variable region inserted in pCR-TNLV2 Lv vector prepared in Example 3, pHAB-KC (KCTC 10230BP, Korean Patent Laid-open Publication No. 2004-12268) expression vector containing the gene encoding the light chain constant region of the human antibody was employed.

First, in order to insert gene TNLV2 encoding the light chain variable region of the humanized antibody into expression vector pHAB-KC, pCR-TNLV2 Lv was treated with HindIII/BsiWI (BioLabs, Inc., USA) at 37° C. for 2 hrs, electrophoresed on a 1.5% agarose gel and stained with etidium bromide (EtBr), and an about 400 bp fragment of the gene was observed.

Figure 6:
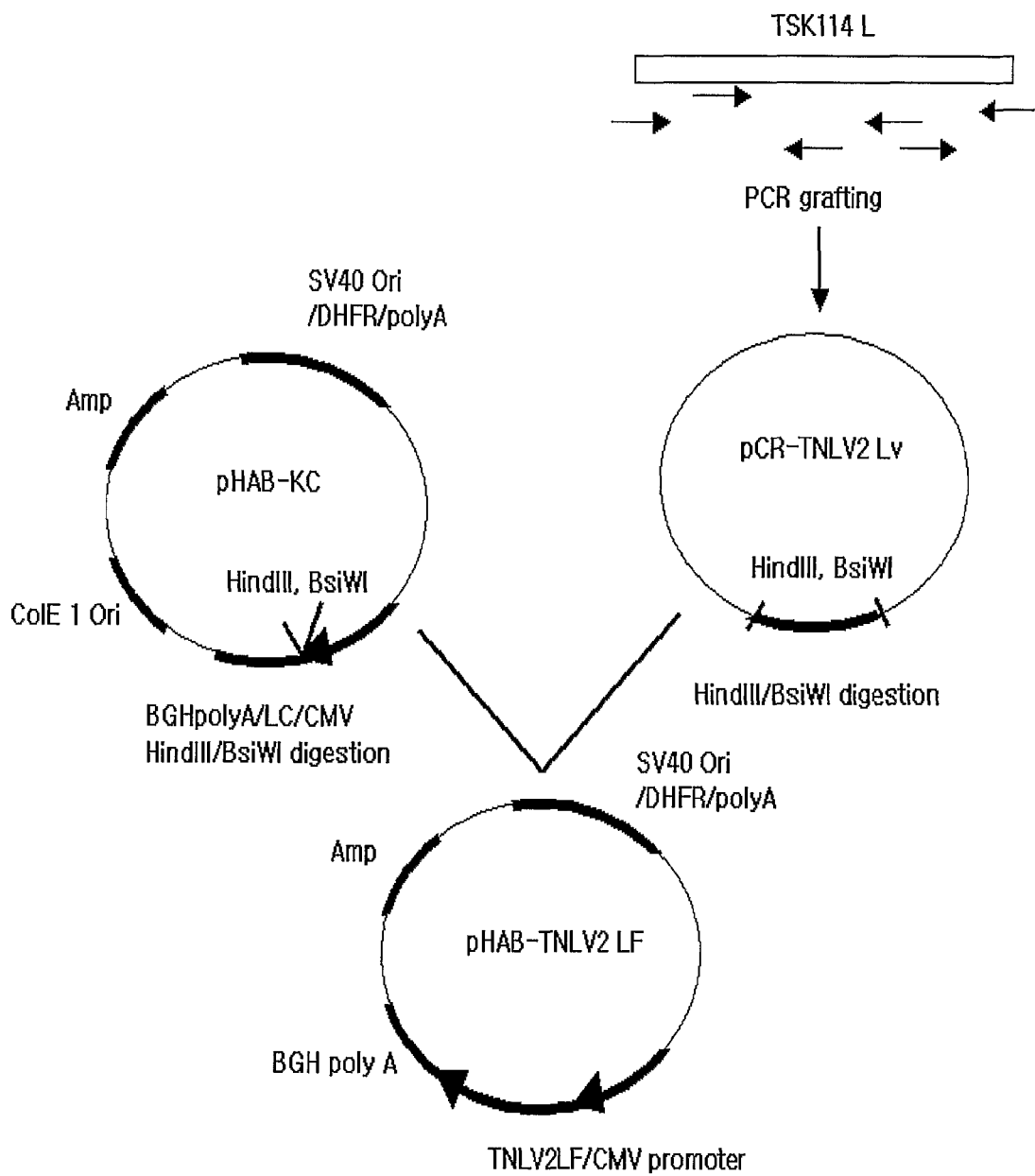
FIG. 6: Schematic diagram showing the process for preparing vector pHAB-TNLV2 LF expressing the light chain of the inventive humanized antibody.

In the same manner as described above, expression vector pHAB-KC was also treated with HindIII/BsiWI, and an about 6.5 kb fragment of the digested vector was observed. After then, the gene fragments observed were recovered from the gels using QIAgel extraction kit (Qiagen, USA), treated with T4 DNA ligase (BioLabs, Inc., USA) at 16° C. overnight, and transformed into E. coli TOP10F' to obtain a transformant. The transformant was cultured in an LB medium supple- The full-length light chain gene of the humanized antibody thus prepared was designated TNLV2 LF. Further, the expression vector inserted with TNLV2 LF was designated pHAB-TNLV2 LF (FIG. 6), and transformed into E. coli TOP10F' to obtain a transformant, which was deposited on Sep. 1, 2004 with the Korean Collection for Type Cultures (KCTC) under the accession number KCTC 10690BP.

Figure 7:
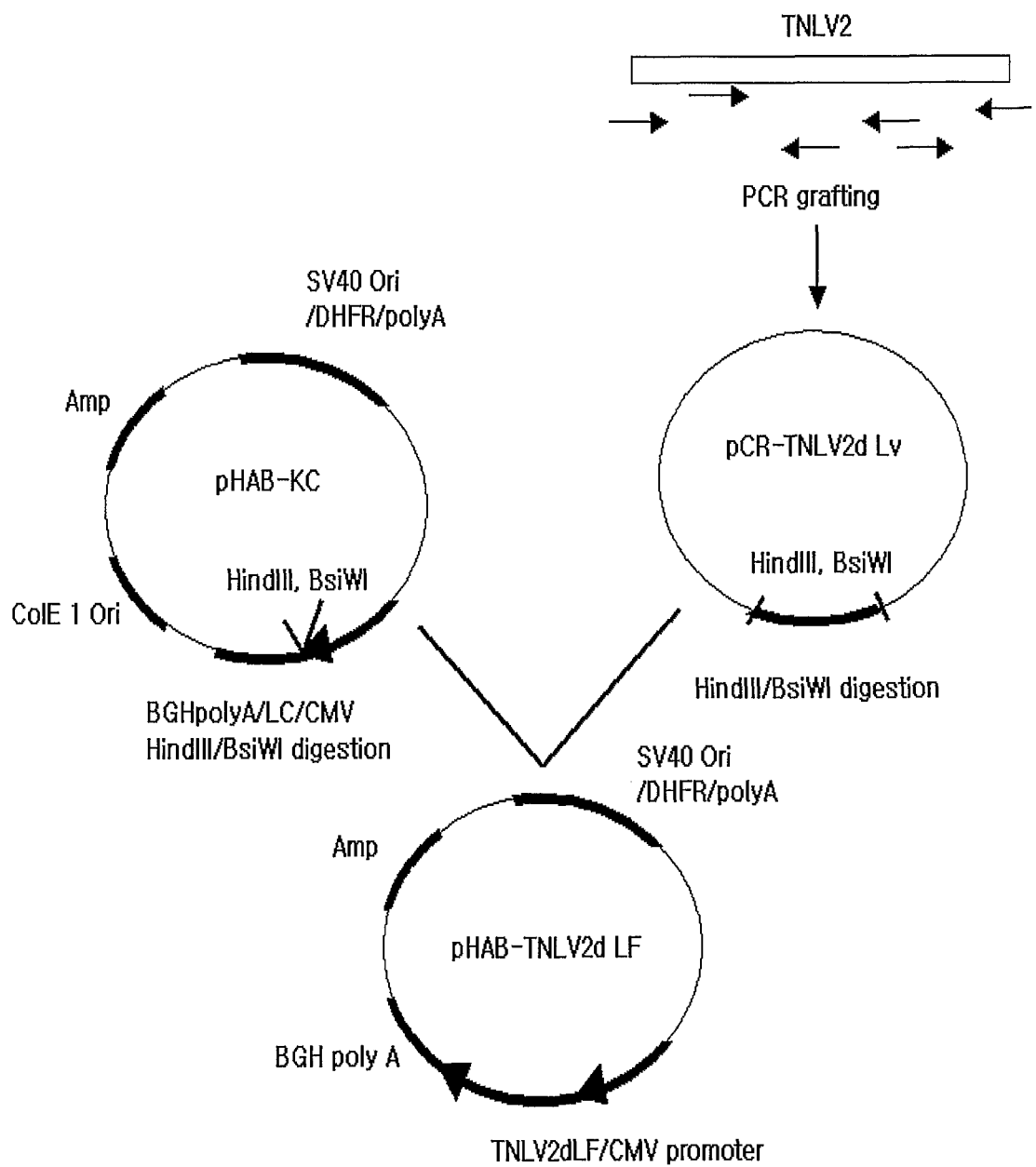
FIG. 7: Schematic diagram showing the process for preparing vector pHAB-TNLV2d LF expressing the light chain of the inventive humanized antibody.

In the same manner as described above, a full-length light chain gene of the humanized antibody was prepared using TNLV2d gene, and the full-length light chain gene of the humanized antibody thus prepared was designated TNLV2d LF. Further, the expression vectors inserted with TNLV2d LF was designated pHAB-TNLV2d LF (FIG. 7), and transformed into E. coli TOP10F' to obtain a transformant, which was deposited on Jun. 13, 2005, with the Korean Collection for Type Cultures (KCTC) under the accession number KCTC 10817BP.

EXAMPLE 5

Transformation of a Humanized Antibody into CHO Cell Lines

In order to measure the humanized antibody activity in animal cells, heavy chain expression vector pHAB-TNHV2 HF prepared in Example 2 and light chain expression vector pHAB-TNLV2 LF prepared in Example 4 were transfected into CHO cell line (ATCC CRL-9096, USA) as follows.

First, CHO cells were grown in DMEM/F12 medium (JRH Inc., USA) supplemented with 2.0 g/l of sodium bicarbonate (Sigma, USA) and 10% heat inactivated FBS (Gibco BRL, USA) in a 37° C. humidified $CO_2$ incubator for 2 to 3 days. The cultured cells were harvested by centrifuging the culture solution at 1,200 rpm and room temperature (25° C.) for 5 min, stained with 0.4% trypan blue (Gibco BRL, USA), and counted with a hematocytometer. The cells were seeded to a T-75 flask in an amount of about $3 \times 10^5$ cells to be sub-cultured.

The seeded CHO cells were allowed to proliferate until they occupied the flask's surface by a density of 60 to 90%. 10 μg of pHAB-TNHV2 HF, 10 μg of pHAB-TNLV2 LF and 80 μl of GenePORTER solution (GTS, USA) for transfection were mixed with 5 ml of DMEM/F12 (serum-free) medium. After the mixture was kept at room temperature for 10 to 45 min, the culture medium was removed from the flask, and the sub-cultured CHO cells were incubated with the mixture in a 37° C. humidified $CO_2$ incubator for about 3 to 5 hrs, to obtain a transfectant designated CHO-YHB1406.

In accordance with the same manner as described above, heavy chain expression vector pHAB-TNHV2k HF and light chain expression vector pHAB-TNLV2 LF, heavy chain expression vector pHAB-TNHV2k HF and light chain expression vector pHAB-TNLV2d LF, or heavy chain expression vector pHAB-TNHV1k HF and light chain expression vector pHAB-TNLV2d LF, which were prepared in Examples 2 and 4, respectively, were transfected into CHO cells to obtain transfectants, which were designated CHO-YHB1411, CHO-YHB1411-2, and CHO-YHB1406-2, respectively.

EXAMPLE 6

Purification of a Humanized Antibody

The transfectant CHO-YHB1406 cells obtained in Example 5 were seeded to a T-75 flask containing a DMEM/F12 medium supplemented with 10% fetal bovine serum in an amount of $2 \times 10^5$ cells, and the flask was incubated in a 37° C. humidified $CO_2$ incubator for 7 days to express the humanized antibody. The culture medium was harvested, centrifuged and filtered to obtain a cell-free culture solution comprising antibodies.

In order to purify the humanized antibody from the solution, sepharose 4 Fast flow columns conjugated with protein-A (Pharmacia) and goat anti-human Immunoglobulin G (Zymed Laboratories Inc., USA), respectively, were employed. The culture medium comprising antibodies was applied to protein-A conjugated sepharose 4 Fast flow column to allow the humanized antibody to bind with protein-A, and a glycine buffer (pH 2.5) was introduced into the column to elute the humanized antibody. Then, the eluate was neutralized by mixing with 1 M Tris-Cl (pH 8.0) at a volume ratio of 1:10, and subjected to sepharose 4 Fast flow column conjugated with goat anti-human IgG to allow the column to specifically capture the antibody protein.

The humanized antibody was eluted according to the same method as described above, and the purified humanized antibody was designated YHB1406.

In accordance with the same manner as described above, the transfectants, CHO-YHB1411, CHO-YHB1411-2 and CHO-YHB1406-2, prepared in Example 5 were cultured and the produced antibodies therefrom were purified, respectively, to obtain the purified humanized antibodies designated YHB1411, YHB1411-2 and YHB1406-2, respectively.

Figure 8:
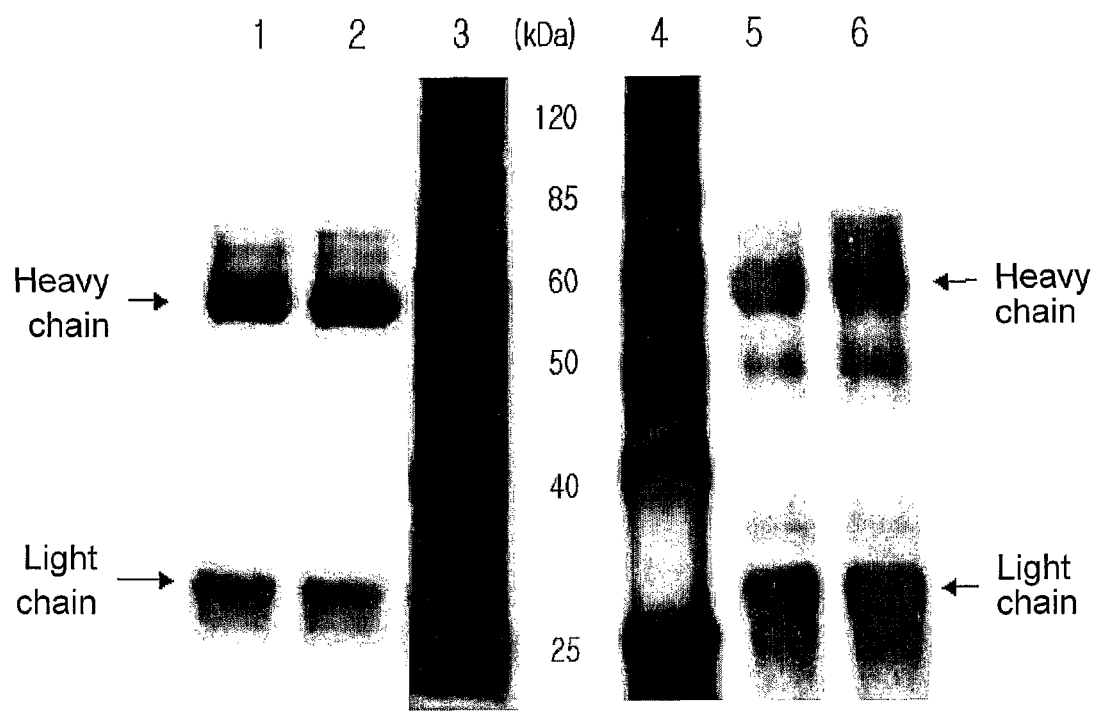
FIG. 8: SDS-PAGE result of the inventive humanized antibody produced in an animal cell and purified thereafter.

As a result of analyzing the purified humanized antibodies with SDS-PAGE, bands of about 50 kDa and about 25 kDa were observed, which were identified as the heavy chain and light chain of the humanized antibody, respectively (FIG. 8).

EXAMPLE 7

Measurement of Antigen Binding Affinity of a Humanized Antibody to hTNF-α

The humanized antibodies purified in Example 6 were quantified with competitive ELISA, and their antigen-binding activities were analyzed by using a recombinant hTNF-α (Biosource, USA). For antibody quantification, 100 ng of goat anti-human immunoglobulin G.A.M (Zymed Laboratories Inc., USA) was distributed into each well of a microplate (Dynatech Laboratories Inc., USA) and the well plate was kept at 4° C. overnight to coat it with the immunoglobulin. At this time, mouse monoclonal antibody TSK114 was used as a control.

In order to measure an antigen-binding affinity of the humanized antibody to recombinant hTNF-α antigen, antigen solutions (100 μl each) having various concentrations ranging from $10^{-11}$ to $10^{-7}$ M were mixed with 5 ng of mouse monoclonal antibody TSK114, humanized antibodies YHB1406, YHB1411, YHB1406-2, and YHB1411-2, respectively, and reacted at 37° C. for 2 hrs. Each of the reactants was added to the well plate coated with 0.4 μg of the antigen and the well plate was kept at 37° C. for about 1.5 hrs. A goat anti-human polyclonal antibody (BioRad, USA) conjugated with horseradish peroxidase was diluted at a ratio of 1:1000 and 100 μl of the diluted antibody solution was added to each well. The well plate was kept at 37° C. for 1 hr. After the reaction was completed, the optical density of each well was measured using a horseradish peroxidase substrate kit (Bio-Rad, USA).

Concentrations of the antibody bound to the antigen and the unbound antibody were calculated from the measured optical density, and antigen-binding affinity of the humanized antibodies were determined therefrom (Friguet B. et al., *J. Immunol. Meth.*, 77: 305-319, 1985). The results are shown in Table 3 and FIG. 9.

TABLE 3

| Antigen | Antigen binding affinity (Kd) |
| --- | --- |
| Mouse antibody TSK114 | $1.4 \times 10^{-10}$ M |
| Humanized antibody YHB1406 | $2.2 \times 10^{-10}$ M |
| Humanized antibody YHB1411 | $2.0 \times 10^{-10}$ M |
| Humanized antibody YHB1411-2 | $2.0 \times 10^{-10}$ M |
| Humanized antibody YHB1406-2 | $2.9 \times 10^{-10}$ M |

Figure 9:
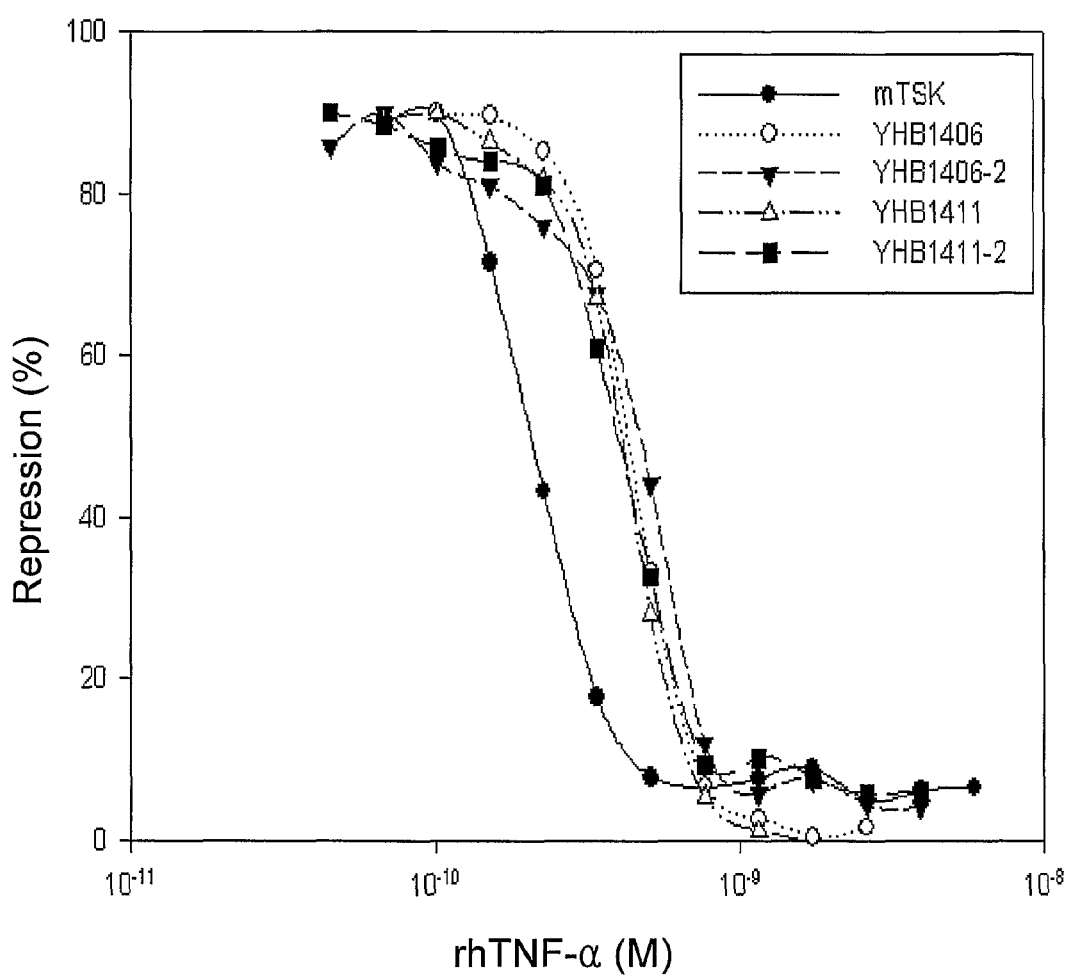
FIG. 9: Graph showing the binding affinities for TNF-α of a mouse monoclonal antibody and the inventive humanized antibodies.

As can be seen in Table 3 and FIG. 9, the antigen binding affinities of humanized antibodies YHB1406, YHB1411, YBB1411-2, and YHB1406-2 were similar to that of mouse monoclonal antibody TSK114.

EXAMPLE 8

Test of In Vitro Antigen Neutralization Capability of the Humanized Antibody

The capabilities of the inventive humanized antibodies for neutralizing hTNF-α antigen in vitro were determined by employing WHEI 164 cell line (ATCC CRL-1751, USA), as follows (Khabar KSA et al., *Immunol. Lett.* 46; 107-110, 1995).

Mouse monoclonal antibody TSK114, and humanized antibodies YHB1406, YHB1411, YHB1411-2 and YHB1406-2 were diluted in PBS buffer to various concentrations ranging from 0.024 ng/mL to 1.0 ug/mL, respectively, and each 100 ul of the resulting dilutions was added to the wells of a 96-well culture plate. 50 ul of hTNF-α solution (100 pg/mL) was added to each well and a reaction was carried out at 37° C. for 1 hr. Then, 50 ul of WHEI 164 cell lines ($1\times10^6$ cells/ml) treated with 2 ug/ml actinomycin D (Sigma, USA) was added to each well.

The cells were cultured at 37° C. for 24 hrs, and 100 ul of the culture solution was removed. 20 ul of a solution of methyl thiazole tetrazolium (MTT, Sigma, USA) diluted in PBS buffer to a concentration of 5 mg/mL was added to each well of the culture plate, and the plate was incubated at 37° C. for 4 hrs for color development. Then, 100 ul of 0.1N HCl-10% SDS solution (Sigma, USA) was added to each well to completely dissolve the colored precipitate, and the absorbance of each well was measured at 595 nm.

From the absorbance dated obtained above, a curve of survival rate of WHEI 164 cell lines versus antibody concentration was drawn. The concentration of the antibodies inhibiting cell death by 50% ($IC_{50}$) was calculated from the curve, and the result is shown in Table 4.

TABLE 4

Antigen neutralization capabilities of the antibodies

| Antigen | $IC_{50}$ (ng/mL) |
|---|---|
| Mouse monoclonal antibody TSK114 | 4.7 |
| Humanized antibody YHB 1406 | 9.2 |
| Humanized antibody YHB 1411 | 6.7 |
| Humanized antibody YHB 1411-2 | 5.5 |
| Humanized antibody YHB 1406-2 | 6.5 |

As shown in Table 4, $IC_{50}$ of mouse monoclonal antibody (TSK114) was 4.7 ng/mL, and those of the inventive humanized antibodies YHB1406, YHB1411, YHB1411-2 and YHB1406-2 were 9.2 ng/mL, 6.7 ng/mL, 5.5 ng/mL and 6.5 ng/mL, respectively. This result shows that the humanized antibodies have in vitro antigen neutralization capabilities similar to the mouse monoclonal antibody.

EXAMPLE 9

Measurement of Antigen Binding Affinity of a Humanized Antibody to hTNF-α by SPR The binding affinities to hTNF-α of a mouse monoclonal antibody and a humanized antibody were measured by surface plasmon resonance (SPR) method. Specifically, hTNF-α (Biosource, USA) was immobilized on a sensor chip CM5 (Biacore, Sweden) at a concentration of 200 ug/ml, and reacted with 25, 50, 100, 200 and 400 nM of mouse monoclonal antibody TSK114 or humanized antibody YHB1411-2, respectively. Then, association and dissociation constants of the reactions were measured by Biacore2000 (Biacore, Sweden).

From the association and dissociation constants measured above, antigen binding affinities of the antibodies were calculated, and the results are shown in Table 5.

TABLE 5

Comparison of the binding affinities to hTNF-α of the mouse monoclonal antibody and humanized antibody

| Antibody | Association constant ($k_{on}$, $M^{-1}s^{-1}$) | Dissociation constant ($k_{off}$, $s^{-1}$) | Antigen binding affinity (Kd, M) |
|---|---|---|---|
| TSK114 | $4.12 \times 10^4$ | $2.39 \times 10^{-7}$ | $5.79 \times 10^{-12}$ |
| YHB1411-2 | $3.96 \times 10^4$ | $6.80 \times 10^{-8}$ | $1.71 \times 10^{-12}$ |

As shown in Table 5, the inventive humanized antibody YHB1411-2 exhibited a high antigen binding affinity of picomole level ($10^{-12}$M) and a low dissociation constant. Further, the antigen binding affinity of humanized antibody YHB1411-2 was higher by about 3 folds than that of mouse monoclonal antibody TSK114.

While the invention has been described with respect to the above specific embodiments, it should be recognized that various modifications and changes may be made to the invention by those skilled in the art which also fall within the scope of the invention as defined by the appended claims.

What is claimed is:

1. A humanized antibody specific for human tumor necrosis factor-α (hTNF-α), comprising:
   a) a heavy chain variable region having the amino acid sequence of SEQ ID NO: 36, 37 or 38;
   b) a light chain variable region having the amino acid sequence of SEQ ID NO: 39 or 40;
   c) a heavy chain constant region identical to that of a human antibody; and
   d) a light chain constant region identical to that of a human antibody.

2. The humanized antibody of claim 1, wherein the antigen binding affinity (Kd) of the antibody ranges from $1\times10^{-9}$ M to $1\times10^{-13}$ M, which is determined by competitive ELISA.

3. The humanized antibody of claim 1, wherein the dissociation constant ($K_{off}$) of the antibody ranges from $1\times10^{-6}$ s$^{-1}$ to $1\times10^{-9}$ s$^{-1}$, which is determined by surface plasmon resonance (SPR).

4. The humanized antibody of claim 1, wherein the heavy chain variable region of the antibody is encoded by a DNA having a nucleotide sequence of SEQ ID NO: 31, 32 or 33.

5. The humanized antibody of claim 1, wherein the light chain variable region of the antibody is encoded by a DNA having the nucleotide sequence of SEQ ID NO: 34 or 35.

6. A pharmaceutical composition comprising the humanized antibody of claim 1, for treating a hTNF-α related disease selected from the group consisting of: rheumatoid arthritis, Crohn's disease, psoriatic arthritis, psoriasis, septicemia, asthma, Wegener's granulomatosis, inflammation, and ankylosing spondylitis.

* * * * *

SEQUENCE LISTING

<160> NUMBER OF SEQ ID NOS: 50

<210> SEQ ID NO 1
<211> LENGTH: 40
<212> TYPE: DNA
<213> ORGANISM: Artificial Sequence
<220> FEATURE:
<223> OTHER INFORMATION: primer

<400> SEQUENCE: 1
aaagcttatg gattgggtgt ggaacttgct attcctgatg        40

<210> SEQ ID NO 2
<211> LENGTH: 33
<212> TYPE: DNA
<213> ORGANISM: Artificial Sequence
<220> FEATURE:
<223> OTHER INFORMATION: primer

<400> SEQUENCE: 2
cctggagcgt cagtcaaggt ctcctgcaag gct					33

<210> SEQ ID NO 3
<211> LENGTH: 36
<212> TYPE: DNA
<213> ORGANISM: Artificial Sequence
<220> FEATURE:
<223> OTHER INFORMATION: primer

<400> SEQUENCE: 3
cttgcaggag accttgactg acgctccagg cttctt					36

<210> SEQ ID NO 4
<211> LENGTH: 39
<212> TYPE: DNA
<213> ORGANISM: Artificial Sequence
<220> FEATURE:
<223> OTHER INFORMATION: primer

<400> SEQUENCE: 4
gtgaggcagg ctccaggaca gggtttagag tggatgggc					39

<210> SEQ ID NO 5
<211> LENGTH: 45
<212> TYPE: DNA
<213> ORGANISM: Artificial Sequence
<220> FEATURE:
<223> OTHER INFORMATION: primer

<400> SEQUENCE: 5
gcccatccac tctaaaccct gtcctggagc ctgcctcacc cagtt					45

<210> SEQ ID NO 6
<211> LENGTH: 39
<212> TYPE: DNA
<213> ORGANISM: Artificial Sequence
<220> FEATURE:
<223> OTHER INFORMATION: primer

<400> SEQUENCE: 6
ggacgggtta ccatgactag ggacacctct gccagcact					39

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7
ggcagaggtg tccctagtca tggtaacccg tccctt					36

<210> SEQ ID NO 8
<211> LENGTH: 39
<212> TYPE: DNA
<213> ORGANISM: Artificial Sequence
<220> FEATURE:
<223> OTHER INFORMATION: primer

<400> SEQUENCE: 8
gcctatatgg agctcagcag cctcagaagt gaggacacg					39

<210> SEQ ID NO 9
<211> LENGTH: 42
<212> TYPE: DNA

```
<213> ORGANISM: Artificial Sequence
<220> FEATURE:
<223> OTHER INFORMATION: primer

<400> SEQUENCE: 9
cgtgtcctca cttctgaggc tgctgagctc catataggca gt                      42

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
gacacggctg tatattactg tgcaagatat gattcc                             36

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
atcatatctt gcacagtaat atacagccgt gtcctc                             36

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
gtgaggcagg ctccaggaaa gggttta                                       27

<210> SEQ ID NO 13
<211> LENGTH: 27
<212> TYPE: DNA
<213> ORGANISM: Artificial Sequence
<220> FEATURE:
<223> OTHER INFORMATION: primer

<400> SEQUENCE: 13
gcccatccac tctaaaccct ttcctgg                                       27

<210> SEQ ID NO 14
<211> LENGTH: 38
<212> TYPE: DNA
<213> ORGANISM: Artificial Sequence
<220> FEATURE:
<223> OTHER INFORMATION: primer

<400> SEQUENCE: 14
tgggcccttg gtggaggctg aggagactgt gacagtgg                           38

<210> SEQ ID NO 15
<211> LENGTH: 39
<212> TYPE: DNA
<213> ORGANISM: Artificial Sequence
<220> FEATURE:
<223> OTHER INFORMATION: primer

<400> SEQUENCE: 15
tgggcccttg gtggaggctg aggagactgt gagagtggt                          39
```

<210> SEQ ID NO 16
<211> LENGTH: 43
<212> TYPE: DNA
<213> ORGANISM: Artificial Sequence
<220> FEATURE:
<223> OTHER INFORMATION: primer

<400> SEQUENCE: 16
aaagcttatg gatttacaag tgcagatttt cagcttcctg cta                43

<210> SEQ ID NO 17
<211> LENGTH: 29
<212> TYPE: DNA
<213> ORGANISM: Artificial Sequence
<220> FEATURE:
<223> OTHER INFORMATION: primer

<400> SEQUENCE: 17
cataacaata tctcctctgg acattatga                                29

<210> SEQ ID NO 18
<211> LENGTH: 36
<212> TYPE: DNA
<213> ORGANISM: Artificial Sequence
<220> FEATURE:
<223> OTHER INFORMATION: primer

<400> SEQUENCE: 18
gttatgaccc agtctccatc aagcctgtct gcatct                        36

<210> SEQ ID NO 19
<211> LENGTH: 36
<212> TYPE: DNA
<213> ORGANISM: Artificial Sequence
<220> FEATURE:
<223> OTHER INFORMATION: primer

<400> SEQUENCE: 19
agacaggctt gatggagact gggtcataac aatttg                        36

<210> SEQ ID NO 20
<211> LENGTH: 33
<212> TYPE: DNA
<213> ORGANISM: Artificial Sequence
<220> FEATURE:
<223> OTHER INFORMATION: primer

<400> SEQUENCE: 20
gcatctgtag gggaacgggt caccatcacc tgc                           33

<210> SEQ ID NO 21
<211> LENGTH: 33
<212> TYPE: DNA
<213> ORGANISM: Artificial Sequence
<220> FEATURE:
<223> OTHER INFORMATION: primer

<400> SEQUENCE: 21
ggtgatggtg acccgttccc ctacagatgc aga                           33

<210> SEQ ID NO 22
<211> LENGTH: 33
<212> TYPE: DNA
<213> ORGANISM: Artificial Sequence
<220> FEATURE:

-continued

<223> OTHER INFORMATION: primer

<400> SEQUENCE: 22 cagcagaaagc caggatccgc ccccaaactc tgg                33

<210> SEQ ID NO 23
<211> LENGTH: 33
<212> TYPE: DNA
<213> ORGANISM: Artificial Sequence
<220> FEATURE:
<223> OTHER INFORMATION: primer

<400> SEQUENCE: 23
gagtttgggg gcggatcctg gcttctgctg ata                33

<210> SEQ ID NO 24
<211> LENGTH: 33
<212> TYPE: DNA
<213> ORGANISM: Artificial Sequence
<220> FEATURE:
<223> OTHER INFORMATION: primer

<400> SEQUENCE: 24
tctgggaccg atttcacttt cacaatcagc agc                33

<210> SEQ ID NO 25
<211> LENGTH: 33
<212> TYPE: DNA
<213> ORGANISM: Artificial Sequence
<220> FEATURE:
<223> OTHER INFORMATION: primer

<400> SEQUENCE: 25
gctgctgatt gtgaaagtga atcggtccc aga                 33

<210> SEQ ID NO 26
<211> LENGTH: 33
<212> TYPE: DNA
<213> ORGANISM: Artificial Sequence
<220> FEATURE:
<223> OTHER INFORMATION: primer

<400> SEQUENCE: 26
agcagcctgc agcctgaaga tattgccact tat                33

<210> SEQ ID NO 27
<211> LENGTH: 33
<212> TYPE: DNA
<213> ORGANISM: Artificial Sequence
<220> FEATURE:
<223> OTHER INFORMATION: primer

<400> SEQUENCE: 27
agtggcaata tcttcaggct gcaggctgct gat                33

<210> SEQ ID NO 28
<211> LENGTH: 27
<212> TYPE: DNA
<213> ORGANISM: Artificial Sequence
<220> FEATURE:
<223> OTHER INFORMATION: primer

<400> SEQUENCE: 28
ggagtcccat ctcgcttcag tggcagt                       27

```
<210> SEQ ID NO 29
<211> LENGTH: 30
<212> TYPE: DNA
<213> ORGANISM: Artificial Sequence
<220> FEATURE:
<223> OTHER INFORMATION: primer

<400> SEQUENCE: 29
cccactgcca ctgaagcgag atgggactcc                                    30

<210> SEQ ID NO 30
<211> LENGTH: 29
<212> TYPE: DNA
<213> ORGANISM: Artificial Sequence
<220> FEATURE:
<223> OTHER INFORMATION: primer

<400> SEQUENCE: 30
gccaccgtac gtttgatttc caccttggt                                     29

<210> SEQ ID NO 31
<211> LENGTH: 351
<212> TYPE: DNA
<213> ORGANISM: Artificial Sequence
<220> FEATURE:
<223> OTHER INFORMATION: Variable region of humanized heavy chain, TNHV2

<400> SEQUENCE: 31
caggtccagt tggtgcagtc tggacctgag ctgaagaagc ctggagcgtc agtcaaggtc   60
tcctgcaagg cttctggata taccttcaca cactatggaa tgaactgggt gaggcaggct  120
ccaggacagg gtttagagtg gatgggctgg ataaacacca acactggaga gccaagatat  180
gatgaagagt tcaagggacg ggttaccatg actagggaca cctctgccag cactgcctat  240
atggagctca gcagcctcag aagtgaggac acggctgtat attactgtgc aagatatgat  300
tccaggggat tgactgctg gggccaaggc accactgtca cagtctcctc a            351

<210> SEQ ID NO 32
<211> LENGTH: 351
<212> TYPE: DNA
<213> ORGANISM: Artificial Sequence
<220> FEATURE:
<223> OTHER INFORMATION: Variable region of humanized heavy chain,
      TNHV2k

<400> SEQUENCE: 32
caggtccagt tggtgcagtc tggacctgag ctgaagaagc ctggagcgtc agtcaaggtc   60
tcctgcaagg cttctggata taccttcaca cactatggaa tgaactgggt gaggcaggct  120
ccaggaaagg gtttagagtg gatgggctgg ataaacacca acactggaga gccaagatat  180
gatgaagagt tcaagggacg ggttaccatg actagggaca cctctgccag cactgcctat  240
atggagctca gcagcctcag aagtgaggac acggctgtat attactgtgc aagatatgat  300
tccaggggat tgactgctg gggccaaggc accactgtca cagtctcctc a            351

<210> SEQ ID NO 33
<211> LENGTH: 351
<212> TYPE: DNA
<213> ORGANISM: Artificial Sequence
<220> FEATURE:
<223> OTHER INFORMATION: Variable region of humanized heavy chain,
      TNHV1k

<400> SEQUENCE: 33
```

```
caggtccagt tggtgcagtc tggacctgag ctgaagaagc ctggagcgtc agtcaaggtc      60
tcctgcaagg cttctggata taccttcaca cactatggaa tgaactgggt gaggcaggct     120
ccaggaaagg gtttagagtg gatgggctgg ataaacacca acactggaga gccaagatat     180
gatgaagagt tcaagggacg ggttaccatg actaggaca cctctgccag cactgcctat      240
atggagctca gcagcctcag aagtgaggac acggctgtat attactgtgc aagatatgat     300
tccaggggat tgactgctg gggccaaggc accactctca cagtctcctc a               351
```

<210> SEQ ID NO 34
<211> LENGTH: 327
<212> TYPE: DNA
<213> ORGANISM: Artificial Sequence
<220> FEATURE:
<223> OTHER INFORMATION: Variable region of humanized light chain,
      TNLV2

<400> SEQUENCE: 34

```
caaattgtta tgacccagtc tccatcaagc ctgtctgcat ctgtagggga acgggtcacc      60
atcacctgca ctgccagctc aagtataagt tacaattact tcactggtA tcagcagaag     120 ccaggatccg cccccaaact ctggatttat agctcatcca atctggcttc tggagtccca     180
tctcgcttca gtggcagtgg gtctgggacc gatttcactt tcacaatcag cagcctgcag     240
cctgaagata ttgccactta ttactgccac cagtatgagc gttccccgtg acgttcggt      300 ggaggcacca aggtggaaat caaacgt                                          327
```

<210> SEQ ID NO 35
<211> LENGTH: 327
<212> TYPE: DNA
<213> ORGANISM: Artificial Sequence
<220> FEATURE:
<223> OTHER INFORMATION: Variable region of humanized light chain,
      TNLV2d

<400> SEQUENCE: 35

```
gatattgtta tgacccagtc tccatcaagc ctgtctgcat ctgtagggga acgggtcacc      60
atcacctgca ctgccagctc aagtataagt tacaattact tcactggtA tcagcagaag     120 ccaggatccg cccccaaact ctggatttat agctcatcca atctggcttc tggagtccca     180
tctcgcttca gtggcagtgg gtctgggacc gatttcactt tcacaatcag cagcctgcag     240
cctgaagata ttgccactta ttactgccac cagtatgagc gttccccgtg acgttcggt      300 ggaggcacca aggtggaaat caaacgt                                          327
```

<210> SEQ ID NO 36
<211> LENGTH: 117
<212> TYPE: PRT
<213> ORGANISM: Artificial Sequence
<220> FEATURE:
<223> OTHER INFORMATION: Variable region of humanized heavy chain,
      TNHV2

<400> SEQUENCE: 36

Gln Val Gln Leu Val Gln Ser Gly Pro Glu Leu Lys Lys Pro Gly Ala
 1               5                  10                  15

Ser Val Lys Val Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Met
        35                  40                  45

Gly Trp Ile Asn Thr Asn Thr Gly Glu Pro Arg Tyr Asp Glu Glu Phe

```
                50                  55                  60
Lys Gly Arg Val Thr Met Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Ser Arg Gly Phe Asp Cys Trp Gly Gln Gly Thr Thr
                100                 105                 110

Val Thr Val Ser Ser
        115

<210> SEQ ID NO 37
<211> LENGTH: 117
<212> TYPE: PRT
<213> ORGANISM: Artificial Sequence
<220> FEATURE:
<223> OTHER INFORMATION: Variable region of humanized heavy chain,
      TNHV2k

<400> SEQUENCE: 37

Gln Val Gln Leu Val Gln Ser Gly Pro Glu Leu Lys Lys Pro Gly Ala
  1               5                  10                  15

Ser Val Lys Val Ser Cys Lys Ala Ser Gly Tyr Thr Phe Thr His Tyr
                 20                  25                  30

Gly Met Asn Trp Val Arg Gln Ala Pro Gly Lys Gly Leu Glu Trp Met
             35                  40                  45

Gly Trp Ile Asn Thr Asn Thr Gly Glu Pro Arg Tyr Asp Glu Glu Phe
         50                  55                  60

Lys Gly Arg Val Thr Met Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Ser Arg Gly Phe Asp Cys Trp Gly Gln Gly Thr Thr
                100                 105                 110

Val Thr Val Ser Ser
        115

<210> SEQ ID NO 38
<211> LENGTH: 117
<212> TYPE: PRT
<213> ORGANISM: Artificial Sequence
<220> FEATURE:
<223> OTHER INFORMATION: Variable region of humanized heavy chain,
      TNHV1k

<400> SEQUENCE: 38

Gln Val Gln Leu Val Gln Ser Gly Pro Glu Leu Lys Lys Pro Gly Ala
  1               5                  10                  15

Ser Val Lys Val Ser Cys Lys Ala Ser Gly Tyr Thr Phe Thr His Tyr
                 20                  25                  30

Gly Met Asn Trp Val Arg Gln Ala Pro Gly Lys Gly Leu Glu Trp Met
             35                  40                  45

Gly Trp Ile Asn Thr Asn Thr Gly Glu Pro Arg Tyr Asp Glu Glu Phe
         50                  55                  60

Lys Gly Arg Val Thr Met Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Ser Arg Gly Phe Asp Cys Trp Gly Gln Gly Thr Thr
```

```
                        100                 105                 110
Leu Thr Val Ser Ser
        115

<210> SEQ ID NO 39
<211> LENGTH: 109
<212> TYPE: PRT
<213> ORGANISM: Artificial Sequence
<220> FEATURE:
<223> OTHER INFORMATION: Variable region of humanized light chain, TNLV2

<400> SEQUENCE: 39

Gln Ile Val Met Thr Gln Ser Pro Ser Ser Leu Ser Ala Ser Val Gly
 1               5                  10                  15

Glu Arg Val Thr Ile Thr Cys Thr Ala Ser Ser Ser Ile Ser Tyr Asn
            20                  25                  30

Tyr Phe His Trp Tyr Gln Gln Lys Pro Gly Ser Ala Pro Lys Leu Trp
        35                  40                  45

Ile Tyr Ser Ser Ser Asn Leu Ala Ser Gly Val Pro Ser Arg Phe Ser
    50                  55                  60

Gly Ser Gly Ser Gly Thr Asp Phe Thr Phe Thr Ile Ser Ser Leu Gln
 65                  70                  75                  80

Pro Glu Asp Ile Ala Thr Tyr Tyr Cys His Gln Tyr Glu Arg Ser Pro
                85                  90                  95

Trp Thr Phe Gly Gly Gly Thr Lys Val Glu Ile Lys Arg
            100                 105

<210> SEQ ID NO 40
<211> LENGTH: 109
<212> TYPE: PRT
<213> ORGANISM: Artificial Sequence
<220> FEATURE:
<223> OTHER INFORMATION: Variable region of humanized light chain,
      TNLV2d

<400> SEQUENCE: 40

Asp Ile Val Met Thr Gln Ser Pro Ser Ser Leu Ser Ala Ser Val Gly
 1               5                  10                  15

Glu Arg Val Thr Ile Thr Cys Thr Ala Ser Ser Ser Ile Ser Tyr Asn
            20                  25                  30

Tyr Phe His Trp Tyr Gln Gln Lys Pro Gly Ser Ala Pro Lys Leu Trp
        35                  40                  45

Ile Tyr Ser Ser Ser Asn Leu Ala Ser Gly Val Pro Ser Arg Phe Ser
    50                  55                  60

Gly Ser Gly Ser Gly Thr Asp Phe Thr Phe Thr Ile Ser Ser Leu Gln
 65                  70                  75                  80

Pro Glu Asp Ile Ala Thr Tyr Tyr Cys His Gln Tyr Glu Arg Ser Pro
                85                  90                  95

Trp Thr Phe Gly Gly Gly Thr Lys Val Glu Ile Lys Arg
            100                 105

<210> SEQ ID NO 41
<211> LENGTH: 5
<212> TYPE: PRT
<213> ORGANISM: Mus musculus

<400> SEQUENCE: 41

His Tyr Gly Met Asn
 1               5
```

<210> SEQ ID NO 42
<211> LENGTH: 17
<212> TYPE: PRT
<213> ORGANISM: Mus musculus

<400> SEQUENCE: 42

Trp Ile Asn Thr Asn Thr Gly Glu Pro Arg Tyr Asp Glu Glu Phe Lys
1               5                   10                  15
Gly

<210> SEQ ID NO 43
<211> LENGTH: 8
<212> TYPE: PRT
<213> ORGANISM: Mus musculus

<400> SEQUENCE: 43

Tyr Asp Ser Arg Gly Phe Asp Cys
1               5

<210> SEQ ID NO 44
<211> LENGTH: 12
<212> TYPE: PRT
<213> ORGANISM: Mus musculus

<400> SEQUENCE: 44

Thr Ala Ser Ser Ser Ile Ser Tyr Asn Tyr Phe His
1               5                   10

<210> SEQ ID NO 45
<211> LENGTH: 7
<212> TYPE: PRT
<213> ORGANISM: Mus musculus

<400> SEQUENCE: 45

Ser Ser Ser Asn Leu Ala Ser
1               5

<210> SEQ ID NO 46
<211> LENGTH: 9
<212> TYPE: PRT
<213> ORGANISM: Mus musculus

<400> SEQUENCE: 46

His Gln Tyr Glu Arg Ser Pro Trp Thr
1               5

<210> SEQ ID NO 47
<211> LENGTH: 117
<212> TYPE: PRT
<213> ORGANISM: Mus musculus

<400> SEQUENCE: 47

Gln Val Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr His Tyr
            20                  25                  30

Gly Met Asn Trp Val Lys Gln Ala Pro Gly Glu Gly Leu Lys Trp Met
        35                  40                  45

Gly Trp Ile Asn Thr Asn Thr Gly Glu Pro Arg Tyr Asp Glu Glu Phe
    50                  55                  60

Lys Gly Arg Phe Ala Phe Ser Leu Glu Thr Ser Ala Ser Thr Ala Tyr
65                  70                  75                  80

```
Leu Gln Ile Asn Asn Leu Arg Arg Glu Asp Thr Ala Thr Tyr Phe Cys
                85                  90                  95

Ala Arg Tyr Asp Ser Arg Gly Phe Asp Cys Trp Gly Gln Gly Thr Thr
            100                 105                 110

Leu Thr Val Ser Ser
        115

<210> SEQ ID NO 48
<211> LENGTH: 98
<212> TYPE: PRT
<213> ORGANISM: Homo sapiens

<400> SEQUENCE: 48

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 49
<211> LENGTH: 109
<212> TYPE: PRT
<213> ORGANISM: Mus musculus

<400> SEQUENCE: 49

Gln Ile Val Leu Thr Gln Ser Pro Ala Ile Met Ser Ala Ser Leu Gly
 1               5                  10                  15

Glu Arg Val Thr Met Thr Cys Thr Ala Ser Ser Ser Ile Ser Tyr Asn
            20                  25                  30

Tyr Phe His Trp Tyr Gln Gln Arg Pro Gly Ser Ser Pro Lys Leu Trp
        35                  40                  45

Ile Tyr Ser Ser Ser Asn Leu Ala Ser Gly Val Pro Pro Arg Ile Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr Glu Arg Ser Pro
                85                  90                  95

Trp Thr Phe Gly Gly Gly Thr Lys Leu Glu Ile Lys Arg
            100                 105

<210> SEQ ID NO 50
<211> LENGTH: 95
<212> TYPE: PRT
<213> ORGANISM: Homo sapiens

<400> SEQUENCE: 50

Gln Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
```

-continued

```
                20                  25                  30
Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95
```